United States Patent

Skuballa et al.

[11] 4,235,930
[45] Nov. 25, 1980

[54] NOVEL ACETYLENIC PROSTAGLANDINS AND PROCESSES FOR THE PREPARATION THEREOF

[75] Inventors: Werner Skuballa; Bernd Radüchel; Helmut Vorbrüggen; Walter Elger; Olaf Loge; Ekkehard Schillinger, all of Berlin, Fed. Rep. of Germany

[73] Assignee: Schering, A.G., Berlin and Bergkamen, Fed. Rep. of Germany

[21] Appl. No.: 920,523

[22] Filed: Jun. 29, 1978

[30] Foreign Application Priority Data

Jun. 30, 1977 [DE] Fed. Rep. of Germany ....... 2729960

[51] Int. Cl.³ .................. C07C 177/00; A61K 31/557
[52] U.S. Cl. ............................. 424/305; 260/313.8 P; 260/345.7 P; 260/345.8 P; 260/346.22; 260/347.3; 260/347.4; 260/410; 260/456 R; 260/456 P; 260/448.8 R; 260/556 A; 260/561 R; 542/426; 560/106; 560/121; 560/231; 562/503; 424/317; 424/320; 424/321; 564/98; 564/152
[58] Field of Search .................. 560/121, 231, 106; 562/503; 424/305, 317; 542/426; 260/410, 448.8 R, 456 R, 456 P, 345.7 P, 345.8 P, 347.3, 347.4

[56] References Cited

U.S. PATENT DOCUMENTS 4,073,934  2/1978  Skuballa et al. .................... 424/305

Primary Examiner—Robert Gerstl
Attorney, Agent, or Firm—Millen & White

[57] ABSTRACT

Prostane derivatives of the formula

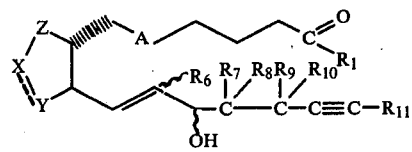

wherein
$R_1$ is the residue $OR_2$ and $R_2$ is hydrogen, alkyl, cycloalkyl, aryl, or a heterocyclic residue; or is $NHR_3$ wherein $R_3$ is an acyl group derived from a hydrocarbon carboxylic or sulfonic acid of up to 15 carbon atoms;
A is —$CH_2$—$CH_2$— or cis—CH=CH—
Z is carbonyl or

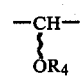

wherein the $OR_4$ group can be in the α- or β-position and $R_4$ is H or a hydroxy-protective group
X====Y is

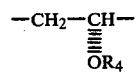

wherein $R_4$ is as defined above, —$CH_2$—$CH_2$— or —$CH_2$—CH— wherein $R_5$ is alkyl or 1-5 carbon atoms, if Z is $R_5$ carbonyl or

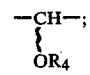

X====Y represents —CH=CH— if Z is carbonyl:
$R_6$, $R_7$, $R_8$, $R_9$ and $R_{10}$ each independently is hydrogen or an alkyl group of 1–5 carbon atoms; and
$R_{11}$ is alkyl of 1–5 carbon atoms;
and if $R_2$ is hydrogen, the salts thereof with physiologically compatible bases are prostaglandins having prolonged duration of activity and increased selectivity of effectiveness.

29 Claims, No Drawings

NOVEL ACETYLENIC PROSTAGLANDINS AND PROCESSES FOR THE PREPARATION THEREOF

BACKGROUND OF THE INVENTION

The present invention relates to novel prostan-18-yne derivatives, processes for their preparation, as well as their use as medicinal agents.

DOS's [German Unexamined Laid-Open Applications] Nos. 2,517,771 (U.S. Pat. No. 4,073,934); 2,517,801 (Great Britain Pat. No. 1,458,315) and 2,118,686 (U.S. Pat. No. 3,775,462) disclose prostane derivatives having an acetylenic grouping in the 16-position.

From the extremely voluminous prior art existing in the realm of the prostaglandins and their analogs, in addition to the above DOS's, it is also known that this class of compounds, due to the biological and pharmacological properties displayed thereby, is suitable for the treatment of mammals, including humans. However, their use as medicinal agents frequently poses difficulties. Most of the natural prostaglandins possess a duration of activity which is too short for therapeutic purposes, since they are too rapidly degraded metabolically by various enzymatic processes. Therefore, the production of derivatives of prostanoic acid has gained great importance. All structural alterations have the objective of prolonging the duration of effectiveness and increasing the selectivity of their effectiveness.

SUMMARY OF THE INVENTION

Accordingly, it is an object of this invention to provide such improved prostaglandins.

Upon further study of the specification and appended claims, further objects and advantages of this invention will become apparent to those skilled in the art.

These and other objects of this invention have been achieved by providing novel prostane derivatives of Formula I $$\begin{array}{c}\text{(Formula I)}\end{array}$$

wherein
$R_1$ is the residue $OR_2$ and $R_2$ is hydrogen, alkyl, cycloalkyl, aryl, or a heterocyclic residue; or is the residue $NHR_3$ and $R_3$ is an acid residue;
A is $-CH_2-CH_2-$ or cis$-CH=CH-$
Z is carbonyl or $$-\underset{OR_4}{\overset{}{C}H}-$$

wherein the $OR_4$ group can be in the $\alpha$- or $\beta$-position; and $R_4$ is H or a hydroxy protective group
$X=\!=\!=Y$ is $$-CH_2-\underset{OR_4}{\overset{}{\underset{\equiv}{C}H}}-,$$

wherein $R_4$ is as defined above, $-CH_2-CH_2-$ or $$-CH_2-\underset{R_5}{\overset{}{\underset{\equiv}{C}H}}-$$

wherein $R_5$ is alkyl of 1-5 carbon atoms, if Z is carbonyl or $$-\underset{OR_4}{\overset{}{C}H}-;$$

$X=\!=\!=Y$ is $-CH=CH-$ if Z is carbonyl;
$R_6$, $R_7$, $R_8$, $R_9$ and $R_{10}$ each independently is hydrogen or an alkyl group of 1-5 carbon atoms; and
$R_{11}$ is an alkyl group of 1-5 carbon atoms;
and, if $R_2$ is hydrogen, the salts thereof with physiologically compatible bases.

DETAILED DISCUSSION

Suitable alkyl groups $R_2$ are straight-chain or branched alkyl groups of 1-10 carbon atoms, e.g., methyl, ethyl, propyl, butyl, isobutyl, tert-butyl, pentyl, neopentyl, heptyl, hexyl, decyl and the like.

The alkyl groups $R_2$ can optionally be mono- or polysubstituted by halogen, $C_{1-5}$ alkoxy, optionally substituted aryl or aroyl groups, di $C_{1-5}$ alkylamines, and tri $C_{1-5}$ alkylammonium. Suitable such substituents include fluorine, chlorine, bromine, phenyl, dimethylamine, diethylamine, methoxy, ethoxy and the like. Suitable substituted or unsubstituted aryl or aroyl include those aryl groups defined below for $R_2$ and the aroyl groups derived therefrom. Preferred alkyl groups $R_2$ are those of 1-4 carbon atoms in the alkyl chain, e.g., dimethylaminopropyl, isobutyl, butyl, etc.

Suitable aryl groups $R_2$ include substituted as well as unsubstituted aryl groups, e.g., phenyl, 1-naphthyl and 2-naphthyl, each of which can be substituted by 1-3 halogen atoms (F, Cl, Br, I), phenyl, 1-3 alkyl groups each of 1-4 carbon atoms, chloromethyl, fluoromethyl, trifluoromethyl, carboxy, hydroxy, or alkoxy of 1-4 carbon atoms. Substitution in the 3- and 4-positions of the phenyl ring is preferred, for example, by fluorine, chlorine, alkoxy, or trifluoromethyl, or in the 4-position by hydroxy.

Suitable cycloalkyl groups $R_2$ can contain 4-10, preferably 5 or 6 carbon atoms in the ring. The rings can be substituted by alkyl groups each of 1-4 carbon atoms. Suitable examples include cyclopentyl, cyclohexyl, methylcyclohexyl, and adamantyl.

Suitable heterocyclic groups $R_2$ include 5- and 6-membered heterocycles, preferably monocycles, containing at least one hetero atom, preferably nitrogen, oxygen or sulfur, preferably one hetero atom. Suitable examples include 2-furyl, 2-thienyl, 2-pyridyl, 3-pyridyl, 4-pyridyl and others.

Physiologically compatible acid residues are suitable as the acid residue $R_3$. Such acids include hydrocarbon carboxylic or sulfonic acids of up to 15 carbon atoms. Preferred acids are organic carboxylic acids and sulfonic acids of 1-15 carbon atoms of the aliphatic, cycloaliphatic, aromatic or aromatic-aliphatic series. These acids can be saturated, unsaturated and/or polybasic and/or substituted in conventional fashion. Examples of suitable substituents include $C_{1-5}$ alkyl, hydroxy, $C_{1-5}$ alkoxy, oxo, amino or halogen (F, Cl, Br, I).

Suitable such carboxylic acids include: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, benzoic acid substituted by halogen, trifluoromethyl, hydroxy, alkoxy, or carboxy groups, nicotinic acid, isonicotinic acid, furan-2-carboxylic acid, cyclopentylpropionic acid, etc. Especially preferred acyl residues are those of up to 10 carbon atoms. Examples of suitable sulfonic acids include methanesulfonic acid, ethanesulfonic acid, isopropylsulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholino-sulfonic acids.

As is evident from the diverse nature of the illustrative carboxylic and sulfonic acids named above, the exact structure of the acid residue is not critical. Therefore, contemplated equivalents of these preferred hydrocarbon carboxylic and sulfonic acids are those other types of acids named above, e.g., the heterocyclic acids.

Suitable alkyl groups $R_5$, $R_6$, $R_7$, $R_8$, $R_9$, $R_{10}$, $R_{11}$ include straight-chain and branched alkyl residues of 1–5 carbon atoms, such as, for example, methyl, ethyl, propyl, isopropyl, butyl, isobutyl, tert-butyl, pentyl, isopentyl, and neopentyl. The methyl and ethyl groups are preferred.

The hydroxy group in

can be functionally modified, e.g., by etherifying or esterifying.

Suitable ether and acyl residues are conventional and well known to a person skilled in the art, e.g., as disclosed in MC. Ornie Ed., Protective Groups in Organic Chemistry, Plenum Press, N.Y. 1973 which is incorporated by reference herein. Ether residues which can be readily split off are preferred, such as the tetrahydropyranyl, tetrahydrofuranyl, α-ethoxyethyl, trimethylsilyl, dimethyl-tert-butylsilyl, and tri-p-benzylsilyl residues. Suitable acyl residues include those defined in conjunction with $R_3$; the following are included among typical examples: acetyl, propionyl, butyryl and benzoyl.

Suitable for forming salts of the acid group present when $R_2$ is H are the inorganic and organic bases which are known to those skilled in the art for producing physiologically compatible salts.

Suitable examples include alkali metal hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The present invention furthermore relates to a process for the preparation of the novel prostan-18-yne derivatives of Formula I, characterized by conventionally hydrolyzing a compound of Formula II

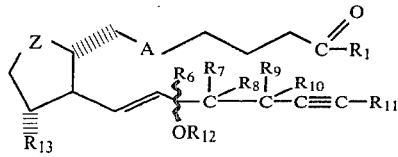

wherein
$R_1$, A, Z, $R_6$, $R_7$, $R_8$, $R_9$, $R_{10}$ and $R_{11}$ are as defined above and
$R_{13}$ is hydrogen, the residue $R_5$ as defined above, hydroxy, or $OR_{12}$— wherein $R_{12}$ is an ether residue which can be readily cleaved.

Suitable examples of ether residues $R_{12}$ include tetrahydropyranyl, tetrahydrofuranyl, α-ethoxyethyl, trimethylsilyl, tribenzylsilyl, and dimethyl-tert-butylsilyl. Especially preferred are tetrahydropyranyl, trimethylsilyl, tribenzylsilyl, and dimethyl-tert-butylsilyl. Optionally, in any desired sequence, a double bond can be introduced in the 10,11-position by splitting off water; a free carboxy group ($R_2=H$) can be esterified or, with the use of a base, can be converted into a physiologically compatible salt; or a 9-keto group can be reduced.

The liberation of the functionally modified hydroxy groups to obtain the compounds of Formula I takes place according to conventional methods. For example, the splitting off of ether blocking groups is accomplished in an aqueous solution of an organic acid, such as, for example, hydrochloric acid. To improve solubility, a water-miscible, inert organic solvent is advantageously added. Suitable organic solvents are, for example, alcohols, such as methanol and ethanol; and ethers, such as dimethoxyethane, dioxane and tetrahydrofuran. The preferred solvent is tetrahydrofuran. The splitting-off step is preferably conducted at temperatures of between 20° and 80° C.

The introduction of the ester group $OR_2$ for $R_1$ wherein $R_2$ is an alkyl group of 1–10 carbon atoms takes place using methods known to those skilled in the art. The 1-carboxy compounds are reacted, for example, with diazohydrocarbons in a conventional manner. The esterification with diazohydrocarbons is effected, for example, by mixing a solution of the diazohydrocarbon in an inert solvent, preferably in diethyl ether, with the 1-carboxy compound in the same or a different inert solvent, for example methylene chloride. After the reaction has ceased in 1–30 minutes, the solvent is removed and the ester is purified in the usual way. Diazoalkanes are either known or can be prepared by following conventional methods [Org. Reactions 8: 389–394 (1954)].

The introduction of the ester group —$OR_2$ for $R_1$ wherein $R_2$ is a substituted or unsubstituted aryl group takes place according to methods known to a person skilled in the art. For example, the 1-carboxy compounds are reacted with the corresponding aryl hydroxy compounds with dicyclohexyl carbodiimide in the presence of a suitable base, for example pyridine or triethylamine, in an inert solvent. Suitable solvents are methylene chloride, ethylene chloride, chloroform, ethyl acetate, tetrahydrofuran, preferably chloroform. The reaction is conducted at temperatures of between $-30°$ and $+50°$ C., preferably at $10°$ C.

The dehydration of the 9-oxo compound wherein the 11-hydroxy group and a 10-position hydrogen atom are split off to obtain a prostaglandin A derivative, can be accomplished under conditions generally known to those skilled in the art. In general, the dehydration takes place in a solution of an organic acid, such as acetic acid, or an inorganic acid, such as hydrochloric acid, or in an acetic anhydride-pyridine mixture at temperatures of between $20°$ and $80°$ C. The reaction is terminated after about 2–17 hours.

The prostaglandin derivatives of Formula I wherein $R_1$ is hydroxy can be converted into salts with the use of suitable amounts of the corresponding inorganic bases by neutralization. For example, a solid inorganic salt is obtained when dissolving the corresponding PG acids in water containing the stoichiometric amount of the base, after the water has been evaporated or after adding a water-miscible solvent, such as alcohol or acetone.

To prepare an amine salt, which is done in a conventional manner, the PG acid is dissolved, for example, in a suitable solvent, e.g. ethanol, acetone, diethyl ether, acetonitrile, or benzene, and at least the stoichiometric amount of the amine is added to this solution. During this step, the salt is obtained ordinarily in the solid form or is isolated in the usual way after evaporation of the solvent.

The compounds of Formula II serving as the starting material, with A being a cis—CH═CH—group, can be prepared by conventionally reacting, in an olefin-forming reaction, an aldehyde of general Formula III

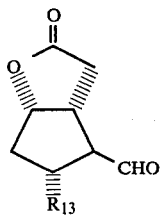

III

[$R_{13}$=OCOPh: E. J. Corey et al. JACS 91, 5675 (1969); E. W. Yankee et al. JACS 96, 5865 (1974); $R_{13}$=H; E. J. Corey et al. JOC 39, 266 (1974)] with a phosphonate of general Formula IV

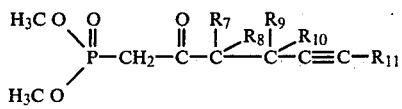

IV wherein $R_7$, $R_8$, $R_9$, $R_{10}$, and $R_{11}$ have the above-indicated meanings, to a ketone of general Formula V

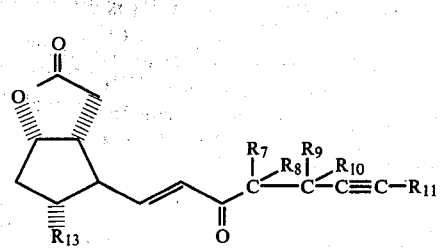

V

After reduction of the 15-keto group with zinc borohydride or sodium borohydride or reaction with alkyl magnesium bromide or alkyl lithium, the epimeric 15α- and 15β-alcohols VI (PG numbering) are obtained, which can be separated if desired:

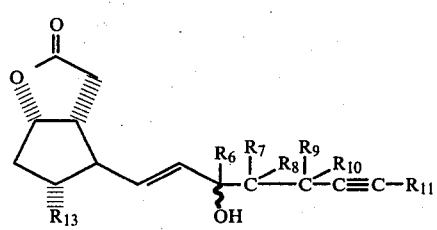

VI

When $R_{13}$ represents an

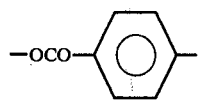

group, it is possible to conduct a saponification with potassium carbonate in methanol to obtain compounds of Formula VI wherein $R_{13}$ represents a hydroxy group. After blockage of the hydroxy groups present, for example with dihydropyran, a reduction is carried out with diisobutyl aluminum hydride to obtain the lactol of Formula VII:

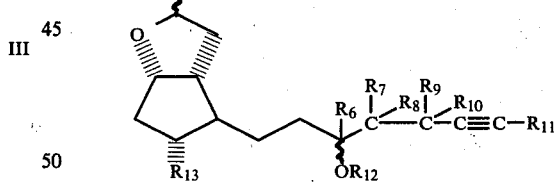

VII

This lactol is converted to compounds of Formula II by a Wittig reaction with a phosphorane of Formula VIII

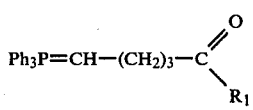

VIII wherein

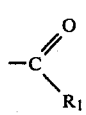

represents a carboxylate group or $R_1$ is an $NHR_3$—group, and by an optionally following oxidation of the 9-hydroxy group with Jones reagent.

Aldehydes of Formula III with $R_{13}$ being an alkyl group are not known and can be prepared in the following way. By stereoselective alkylation with a dialkyl copper reagent of Formula IX,

  IX, wherein $R_{13}$ is an alkyl residue of 1–5 carbon atoms, with an unsaturated ketone of Formula X (P. Crabbé et al., J.C.S. Perkin I 1973, 810)

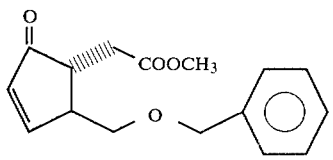  X compounds of Formula XI are obtained:

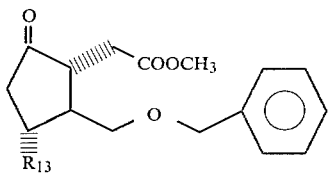  XI

By selective reduction, for example with "L-Selectrid," subsequent cleavage of the benzyl ether by hydrolysis, as well as oxidation of the hydroxymethyl group with, for example, Collins reagent, compounds of Formula III are obtained with $R_{13}$ being an alkyl group.

The compounds of Formula II serving as the starting material, with A being a $-CH_2-CH_2-$group, can be prepared by conventionally converting an aldehyde of Formula III into the diethylacetal, which is then reacted, after reduction with diisobutyl aluminum hydride, to the lactol of Formula XII

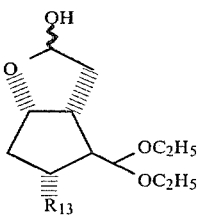  XII wherein $R_{13}$ is alkyl, hydrogen or hydroxy.

Wittig reaction with a phosphorane of Formula VIII, as well as subsequent esterification of free hydroxy groups with an acid chloride or acid anhydride in the presence of a base, for example pyridine, yields compounds of Formula XIII

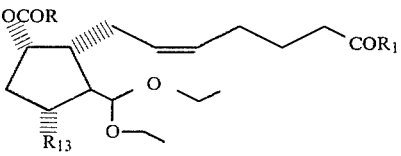  XIII

After hydrogenation of the cis-double bond, splitting of the acetal with, for example, dilute acetic acid, and subsequent olefin-forming reaction with a phosphonate of Formula IV, an unsaturated ketone of Formula XIV is obtained:

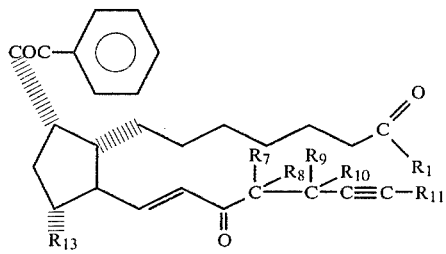  XIV

After reduction of the 15-keto group with zinc borohydride or sodium borohydride, or reaction with alkyl magnesium bromide or alkyl lithium, the epimeric 15α- and 15β-alcohols are obtained which are converted, by etherification with dihydropyran, to the compounds of Formula XV:

XV

After splitting off the ester groups with, for example, potassium carbonate in methanol and optionally regioselective oxidation, for example with oxygen in the presence of platinum, the compounds of Formula II are obtained wherein A is a $-CH_2-CH_2-$group.

The phosphonates of Formula IV are prepared in a conventional manner from an ester of Formula XVI

XVI wherein $R_7$, $R_8$, $R_9$, $R_{10}$, $R_{11}$ are as defined above and $R_{14}$ is an alkyl group of 1–5 carbon atoms, by reacting this ester with the anion of the dimethyl ester of methylphosphonic acid.

The phosphonates of Formula IX are likewise accessible by reacting the dianion of the phosphonate of Formula XVII

XVII with an alkyl halogenide of Formula XVIII

XVIII

The novel prostan-18-yne derivatives of Formula I are valuable pharmacological agents, since they exhibit, with a similar spectrum of activity, a substantially improved (higher specificity) and, above all, essentially longer effectiveness than the corresponding natural prostaglandins. As compared to PGE and PGA derivatives, the novel prostan-18-yne derivatives are distinguished by a higher stability.

Several of the novel compounds have a strong antifertility effect. For the triggering of abortions, substantially lower quantities of the novel prostan-18-yne derivatives are required as compared to the natural prostaglandins.

When recording the isotonic uterus contraction on narcotized rats and on the isolated rat or guinea pig uterus, it can be seen that the compounds of this invention are substantially more active, and their activity is of a longer duration, than in case of the natural prostaglandins. Several of the novel prostanoic acid amides are suitable, after a one-time intrauterine or vaginal administration, to induce menstruation or to interrupt a pregnancy. A portion of the compounds has a luteolytic effect and is suitable for synchronizing the sexual cycle in female mammals, such as monkeys, horses, cattle, pigs, etc.

The high tissue specificity of the compounds of this invention having an antifertility or blood-pressure-lowering effect can be observed in the examination on other smooth-muscle organs, such as, for example, on the guinea pig ileum or on the isolated rabbit trachea, where a substantially lower stimulation is found than in the case of the natural prostaglandins.

Some of the active agents of this invention show, on the isolated rabbit trachea in vitro, even a bronchodilatory effect and strongly inhibit gastric acid secretion. The compounds which have a blood-pressure-lowering effect and diuretic activity additionally show a regulatory effect in case of disturbance of the heart rhythm.

For medical applications, the active agents can be converted into forms suitable for inhaling, for oral, parenteral, or local (e.g., vaginal) administration.

Aerosol solutions are suitable prepared for inhalation purposes.

Suitable for oral application are, for example, tablets, dragees, or capsules.

For parenteral administration, sterile injectable, aqueous or oily solutions are utilized.

Suitable and customary for vaginal application are, for example, suppositories.

The invention, therefore, also concerns medicinal agents containing the compounds of Formula I and the usual excipients and vehicles.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and-/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

For topical applications, the compounds are employed as non-sprayable forms, viscous to semi-solid or solid forms comprising a carrier indigenous to topical application and having a dynamic viscosity preferably greater than water. Suitable formulations include but are not limited to solutions, suspensions, lotions, emulsions, creams, ointments, plasters, powders, linaments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0.001 to 1 wt.%.

Generally, the compounds of this invention are dispensed in unit dosage form comprising 0.01–25 mg. in a pharmaceutically acceptable carrier per unit dosage. Daily dosages are those conventional for other prostaglandins in accordance with conventional considerations such as 0,0001–2 mg/kg of body weight/day.

The effective agents of this invention are to serve, in conjunction with the auxiliary agents known and customary in galenic pharmacy, for example, for the production of preparations to trigger abortion, to regulate the menstrual cycle, to induce labor, or to treat hypertonia.

The temperatures in the following examples are set forth in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, unless otherwise indicated, all parts and percentages are by weight.

EXAMPLE 1

(5Z,13E)-(11R,15R)-16,16-Dimethyl-11,15-dihydroxy-9-oxo-(5,13)-prostadien-18-ynoic Acid 340 mg. of (5Z,13E)-(11R,15R)-16,16-dimethyl-9-oxo-11,15-bis(tetrahydropyran-2-yloxy)-(5,13)-prostadien-18-ynoic acid is agitated for 16 hours at room temperature with 10 ml. of a mixture of glacial acetic acid/water/THF (65/35/10); the mixture is evaporated under vacuum and the residue purified by column chromatography on silica gel. With methylene chloride/5% methanol, 170 mg. of the title compound is obtained as a colorless oil.

IR: 3610, 3400 (broad), 2970, 1740, 1712, 975 cm$^{-1}$.

The starting material for the above compound is prepared as follows:

1(a) Methyl Ester of 2,2-Dimethyl-4-hexynoic Acid

At −20°, 120 ml. of approximately 1.6-molar butyllithium solution in hexane is added dropwise to a solution of 19.6 g. of diisopropylamine in 130 ml. of THF; 10 g. of isobutyric acid and 18 ml. of hexamethylphosphoric triamide are added dropwise to this mixture at −20° to 0°; the mixture is agitated for 35 minutes at room temperature and then, at 0°, 11.7 g. of 1-bromo-2-butyne is added dropwise thereto and the mixture is stirred for 2 hours at room temperature. The reaction solution is stirred into 300 ml. of 10% hydrochloric acid, extracted three times with a mixture of pentane/ether (1+1); the organic extract is washed neutral with water, dried with magnesium sulfate, the solvent is distilled off, and distillation of the residue at 12 torr [mm. Hg] and 124°–125° yields 8.1 g. of 2,2-dimethyl-4-hexynoic acid.

For esterifying purposes, 8 g. of the thus-obtained acid is heated in 13 ml. of methanol with 0.6 ml. of concentrated sulfuric acid under reflux. The mixture is cooled, poured on 40 ml. of ice water, extracted three times with ether, and the organic phase is washed neutral with water, dried with magnesium sulfate; the ether is removed by distillation. After the residue has been distilled at 12 torr and 71°–73°, 6.6 g. of 2,2-dimethyl-4-hexynoic acid methyl ester is obtained as a colorless liquid.

1(b) Dimethyl Ester of 3,3-Dimethyl-2-oxohept-5-ynephosphonic Acid

At −70°, 51.3 ml. of a 1.6-molar butyllithium solution in hexane is added dropwise to a solution of 10.15 g. of methanephosphonic acid dimethyl ester in 165 ml. of tetrahydrofuran (THF); the mixture is stirred for 15 minutes. Then, a solution of 6.3 g. of the ester prepared according to Example 1(a) is added gradually thereto. The mixture is stirred for 4 hours at ice bath temperature, neutralized with acetic acid, and evaporated under vacuum. The remainder is combined with 80 ml. of water, extracted three times with respectively 100 ml. of ether, the organic extract is shaken twice with respectively 20 ml. of water, dried over magnesium sulfate, and evaporated under vacuum. After distillation of the residue at 0.5 torr at 110°, 5.3 g. of phosphonate is obtained as a colorless liquid.

1(c)
(1S,5R,6R,7R)-6-[(E)-3-Oxo-4,4-dimethyl-1-octen-6-ynyl]-7-benzoyloxy-2-oxabicyclo[3,3,0]octan-3-one At room temperature, a solution of 4.1 g. of the phosphonate produced according to Example 1(b) in 14 ml. of dimethoxyethane (DME) is added dropwise to a suspension of 700 mg. of sodium hydride (50% suspension in oil) in 84 ml. of DME (absolute). The mixture is stirred for 2 hours at room temperature under argon. Then the mixture is combined at −20° with a solution of 3.8 g. of (1S,5R,6R,7R)-6-formyl-7-benzoyloxy-2-oxabicyclo[3,3,0]octan-3-one [J. Amer. Chem. Soc. 96: 5865 (1974)] in 42 ml. of DME. The mixture is stirred for 2 hours at −10°, neutralized with acetic acid, diluted with ether, shaken with 4% sodium bicarbonate solution and water, dried over magnesium sulfate, and evaporated under vacuum. After recrystallization from isopropyl ether/methylene chloride, 3.6 g. of the title compound is obtained as colorless crystals, m.p. 73°–74°.

1(d)
(1S,5R,6R,7R)-6-[(E)-(3R)-3-Hydroxy-4,4-dimethyl-1-octen-6-ynyl]-7-benzoyloxy-2-oxabicyclo[3,3,0]octan-3-one and
(1S,5R,6R,7R)-6-[(E)-(3S)-3-Hydroxy-4,4-dimethyl-1-octen-6-ynyl]-7-benzoyloxy-2-oxabicyclo[3,3,0]octan-3-one A solution of 3.35 g. of the ketone obtained according to Example 1(c) in 210 ml. of DME is combined at 5° with 210 ml. of ethereal zinc borohydride solution (preparation: "Neuere Methoden der praeparativen organischen Chemie" [Recent Methods of Preparative Organic Chemistry] IV: 241, Chemie publishers), and the mixture is stirred for 5 hours. After the gentle addition of water, the mixture is diluted with ether, shaken with brine, dried over magnesium sulfate, and evaporated under vacuum. After column chromatography on silica gel with ether/hexane (8+2), 1.7 g. of the α-alcohol (3R-configuration) is first eluted and then 730 mg. of the corresponding β-alcohol (3S-configuration) is obtained, both products in the form of colorless oils.

IR (α-alcohol): 3600, 3520, 2965, 1773, 1718, 1605, 1275, 975 cm$^{-1}$.

IR (β-alcohol): spectrum almost identical to that of the α-alcohol.

1(e)
(1S,5R,6R,7R)-6-[(E)-(3R)-4,4-Dimethyl-3-hydroxy-1-octen-6-ynyl]-7-hydroxy-2-oxabicyclo[3,3,0]octan-3-one A mixture of 1.7 g. of the α-alcohol produced according to Example 1(d) and 595 mg. of potassium carbonate (anhydrous) in 86 ml. of methanol is agitated for 4 hours at 23° under argon. The mixture is then concentrated under vacuum, combined with 86 ml. of 0.1 N hydrochloric acid, extracted three times with ether, the organic extract washed neutral, dried with magnesium sulfate, and evaporated under vacuum. After purification of the residue by column chromatography on silica gel, 1.08 g. of the title compound is obtained with ether as a colorless oil.

IR: 3600, 3430, 2965, 1770, 975 cm$^{-1}$.

1(f)
(1S,5R,6R,7R)-6-[(E)-(3R)-4,4-Dimethyl-3-(tetrahydropyran-2-yloxy)-1-octen-6-ynyl]-7-(tetrahydropyran-2-yloxy)-2-oxabicyclo[3,3,0]octan-3-one 865 mg. of the diol produced by following Example 1(e) is agitated for 30 minutes at 0° with 650 mg. of dihydropyran and 5 mg. of p-toluenesulfonic acid in 18 ml. of methylene chloride. After dilution with methylene chloride, the mixture is shaken with 4% sodium bicarbonate solution and water, dried over magnesium sulfate, and evaporated under vacuum, thus obtaining 1.35 g. of the title compound as a colorless oil.

IR: 2950, 1768, 976 cm$^{-1}$.

1(g)
(2RS,3aR,4R,5R,6aS,3'R)-4-[(E)-4,4-Dimethyl-1-octen-6-ynyl]-2-hydroxy-3',5-bis(tetrahydropyran-2-yloxy)-perhydrocyclopenta[b]furan Under argon, 13.5 ml. of a 20% solution of diisobutyl aluminum hydride in toluene is added dropwise to a solution, cooled to −65°, of 1.35 g. of the bis-THP ether produced according to Example 1(f) in 50 ml. of dry toluene. The mixture is stirred for 30 minutes at −65°, and then the reaction is terminated by the dropwise addition of isopropanol. The mixture is combined with 6 ml. of water, the cooling bath is removed, the mixture stirred for 60 minutes, filtered, and evaporated under vacuum, thus obtaining 1.31 g. of the title compound as a colorless oil.

IR: 3600, 3405, 2950, 980 cm$^{-1}$.

1(h)
(5Z,13E)-(9S,11R,15R)-16,16-Dimethyl-9-hydroxy-11,15-bis(tetrahydropyran-2-yloxy)-5,13-prostadien-18-ynoic Acid At 15°, 21.15 ml. of a solution of methanesulfinylmethyl sodium in absolute DMSO (preparation: 1.5 g. of 50% sodium hydride suspension is dissolved in 30 ml. of absolute DMSO by heating for one hour to 70°) is added dropwise to a solution of 4.87 g. of 4-carboxybutyltriphenylphosphonium bromide in 30 ml. of dry dimethyl sulfoxide (DMSO). The mixture is stirred for 15 minutes at 20°. A solution of 1.27 g. of the lactol prepared by following Example 1(g) in 25 ml. of absolute DMSO is added dropwise to the red ylene solution, and the mixture is agitated for 1.5 hours at 50° under argon. The reaction mixture is poured onto 150 ml. of ice water and extracted three times with ether. The aqueous phase is acidified to pH 5 with 10% citric acid solution and extracted three times with a mixture of ethyl acetate/ether (1+1). The organic phase is shaken with brine, dried over magnesium sulfate, and evaporated under vacuum. Chromatography of the residue on silica gel with pentane/ethyl acetate (4+6) yields 1.03 g. of the title compound as a colorless oil.

1(i)
(5Z,13E)-(11R,15R)-16,16-Dimethyl-9-oxo-11,15-bis(-tetrahydropyran-2-yloxy)-5,13-prostadien-18-ynoic Acid At −20°, 1.2 ml. of Jones reagent is added to a solution of 750 mg. of the compound prepared according to Example 1(h) in 23 ml. of acetone. The mixture is stirred for 30 minutes, the excess reagent is destroyed by the dropwise addition of isopropanol, diluted with ether, washed neutral with brine, dried over magnesium sulfate, and evaporated under vacuum. After purification by preparative layer chromatography on silica gel and elution with ether, 396 mg. of the title compound is obtained as a colorless oil.

IR: 3600, 2950, 1740, 1710, 975 cm$^{-1}$.

EXAMPLE 2
(5Z,13E)-(9S,11R,15R)-16,16-Dimethyl-9,11,15-trihydroxy-5,13-prostadien-18-ynoic Acid 275 mg. of the compound produced according to Example 1(h) is stirred for 16 hours at 20° with 8 ml. of a mixture of glacial acetic acid/water/THF (65/35/10). The mixture is evaporated under vacuum and the residue purified by column chromatography on silica gel. With chloroform/10% methanol, 145 mg. of the title compound is obtained as a colorless oil.

IR: 3600, 3500 (broad), 2930, 1710, 975 cm$^{-1}$.

EXAMPLE 3
(5Z,13E)-(11R,15S,16RS)-11,15-Dihydroxy-9-oxo-16-methyl-(5,13)-prostadien-18-ynoic Acid At 20°, 380 mg. of (5Z,13E)-(11R,15S,16RS)-16-methyl-9-oxo-11,15-bis(tetrahydropyran-2-yloxy)-5,13-prostadien-18-ynoic acid is agitated for 16 hours with 12 ml. of a mixture of glacial acetic acid/water/THF (65/35/10); the mixture is evaporated under vacuum, and the remainder is purified by column chromatography on silica gel. With methylene chloride/5% methanol, 195 mg. of the title compound is obtained as a colorless oil.

IR: 3600, 3400 (broad), 2970, 1740, 1712, 978 cm$^{-1}$.

The starting material for the above compound is prepared as follows:

3(a) Methyl Ester of 2-Methyl-4-hexynoic Acid

At 20° C., 130 ml. of an approximately 1.3-molar butyllithium solution in hexane is added dropwise to a solution of 27.1 g. of diisopropylamine in 130 ml. of THF. At −20° to 0°, 6.6 ml. of propionic acid and 18 ml. of hexamethylphosphoric triamide are added dropwise to this mixture, and the latter is stirred for 35 minutes at room temperature, and then at 0° 11.6 g. of 1-bromo-2-butyne is added dropwise thereto. The mixture is then stirred for 2 hours at room temperature. Then, the reaction mixture is stirred into 300 ml. of 10% hydrochloric acid, extracted three times with a mixture of pentane/ether (1+1), the organic extract is washed neutral with water, dried with magnesium sulfate, and the solvent is removed by distillation. After distilling the remainder in a bulb tube at 12 torr and 114°, 7.8 g. of 2-methyl-4-hexynoic acid is obtained as a colorless liquid.

For purposes of esterification, 7.8 g. of the thus-obtained acid is heated in 13 ml. of methanol with 0.6 ml. of concentrated sulfuric acid under reflux. The mixture is cooled, poured on 50 ml. of ice water, extracted three times with ether, and the organic phase is washed neutral with water, dried with magnesium sulfate, and the ether is removed by distillation. After bulb tube distillation of the remainder at 12 torr and 63°, 6.7 g. of the title compound is obtained as a colorless liquid.

3(b) Dimethyl Ester of 3-Methyl-2-oxohept-5-ynephosphonic Acid

Analogously to Example 1(b), 5.6 g. of the title compound is obtained as a colorless liquid from 6.5 g. of the ester prepared according to Example 3(a) after purification by bulb tube distillation at 0.4 torr and 102°.

3(c)
(1S,5R,6R,7R)-6-[(E)-(4RS)-4-Methyl-3-oxo-1-octen-6-ynyl]-7-benzoyloxy-2-oxabicyclo[3,3,0]octan-3-one In analogy to Example 1(c), 7.9 g. of the phosphonate prepared according to Example 3(b) and 7.6 g. of (1S,5R,6R,7R)-6-formyl-7-benzoyloxy-2-oxabicyclo[3,3,0]octan-3-one yield 7.8 g. of the title compound as a colorless oil.

IR: 2962, 2230, 1773, 1718, 1690, 1625, 1600, 979 cm$^{-1}$.

3(d)
(1S,5R,6R,7R)-6-[(E)-(3S,4RS)-3-Hydroxy-4-methyl-1-octen-6-ynyl]-7-benzoyloxy-2-oxabicyclo[3,3,0]octan-3-one and
(1S,5R,6R,7R)-6-[(E)-(3R,4RS)-3-Hydroxy-4-methyl-1-octen-6-ynyl]-7-benzoyloxy-2-oxabicyclo[3,3,0]octan-3-one At 5°, a solution of 6.6 g. of the ketone obtained according to Example 3(c) in 400 ml. of DME is combined with 400 ml. of ethereal zinc borohydride solution, and the mixture is agitated for 4 hours. After the gentle addition of water, the mixture is diluted with ether, shaken with brine, dried with magnesium sulfate, and evaporated under vacuum. After column chromatography on silica gel with ether/hexane (8+2), there is first eluted 3.2 g. of the α-alcohol (3S-configuration) and then 1.8 g. of the corresponding β-alcohol (3R-configuration) is obtained by elution, both products in the form of colorless oils.

IR (α-alcohol): 3610, 3500, 2965, 1774, 1718, 1605, 1275, 978 cm$^{-1}$.

IR (β-alcohol): spectrum almost identical to that of the α-alcohol.

3(e)
(1S,5R,6R,7R)-6-[(E)-(3S,4RS)-3-Hydroxy-4-methyl-1-octen-6-ynyl]-7-hydroxy-2-oxabicyclo[3,3,0]octan-3-one Analogously to Example 1(e), 1.2 g. of the title compound is produced as a colorless oil from 1.8 g. of the α-alcohol prepared according to Example 3(d) and 610 mg. of potassium carbonate.

IR: 3605, 3450, 2963, 1772, 975 cm$^{-1}$.

3(f)
(1S,5R,6R,7R)-6-[(E)-(3S,4RS)-4-Methyl-3-(tetrahydropyran-2-yloxy)-1-octen-6-ynyl]-7-(tetrahydropyran-2-yloxy)-2-oxabicyclo[3,3,0]-octan-3-one Analogously to Example 1(f), 890 mg. of the diol prepared according to Example 3(e) yields 1.38 g. of the title compound as a colorless oil.

IR: 2955, 1770, 976 cm$^{-1}$.

3(g)
(2RS,3aR,4R,5R,6aS,3'S,4'RS)-4-[(E)-4-Methyl-1-octen-6-ynyl]-2-hydroxy-3',5-bis(tetrahydropyran-2-yloxy)perhydrocyclopenta[b]furan Analogously to Example 1(g), 1.3 g. of the bis-THP ether prepared according to Example 3(f) yields 1.28 g. of the title compound as a colorless oil.

IR: 3610, 3400, 2955, 978 cm$^{-1}$.

3(h)
(5Z,13E)-(9S,11R,15S,16RS)-9-Hydroxy-16-methyl-11,15-bis(tetrahydropyran-2-yloxy)-5,13-prostadien-18-ynoic Acid In analogy to Example 1(h), 1.1 g. of the lactol prepared by following Example 3(g) yields 0.89 g. of the title compound as a colorless oil.

IR: 3600, 2935, 1710, 978 cm$^{-1}$.

3(i)
(5Z,13E)-(11R,15S,16RS)-16-Methyl-9-oxo-11,15-bis(tetrahydropyran-2-yloxy)-5,13-prostadien-18-ynoic Acid Analogously to Example 1(i), 0.8 g. of the compound prepared according to Example 3(h) yields 0.52 g. of the title compound as a colorless oil.

IR: 3600, 2945, 1738, 1710, 976 cm$^{-1}$.

EXAMPLE 4

(5Z,13E)-(9S,11R,15S,16RS)-16-Methyl-9,11,15-trihydroxy-5,13-prostadien-18-ynoic Acid Analogously to Example 2, 310 mg. of the compound prepared according to Example 3(h) yields 160 mg. of the title compound as a colorless oil.

IR: 3610, 3450 (broad), 2935, 1710, 976 cm$^{-1}$.

EXAMPLE 5

(5Z,13E)-(11R,15S)-11,15-Dihydroxy-9-oxo-(5,13)-prostadien-18-ynoic Acid

At room temperature, 430 mg. of (5Z,13E)-(11R,15S)-9-oxo-11,15-bis(tetrahydropyran-2-yloxy)-5,13-prostadien-18-ynoic acid is agitated for 16 hours with 15 ml. of a mixture of glacial acetic acid/water/THF (65/35/10); the mixture is concentrated by evaporation under vacuum, and the residue is purified by column chromatography on silica gel. With chloroform/10% isopropanol, 270 mg. of the title compound is obtained as a colorless oil.

IR: 3600, 3430, 2965, 1740, 1710, 976 cm$^{-1}$.

The starting material for the above compound is produced as follows:

5(a) Dimethyl Ester of 2-Oxohept-5-ynephosphonic Acid

At 24°, a solution of 32 g. of 2-oxopropylphosphonic acid dimethyl ester in 100 ml. of absolute THF is added dropwise to a suspension of 9.2 g. of sodium hydride (50% suspension in oil) in 300 ml. of absolute THF; the mixture is stirred for 1.5 hours and then, at 24°, 183 ml. of a 1.2-molar butyllithium solution in hexane is added dropwise, and the mixture is then stirred for 20 minutes. Thereafter, a solution of 32 g. of 1-bromo-2-butyne in 60 ml. of THF is added at 5° dropwise to this mixture; the latter is agitated for 1 hour, neutralized with 3 N hydrochloric acid, and concentrated under vacuum. The mixture is combined with 50 ml. of brine, extracted three times with respectively 200 ml. of methylene chloride, the organic extract is shaken twice with respectively 50 ml. of brine, dried with magnesium sulfate, and evaporated under vacuum. After bulb tube distillation of the remainder at 0.5 torr and 150°, 22 g. of the title compound is obtained as a colorless liquid.

IR: 3000, 2960, 2915, 2860, 1720, 1260, 1035 cm$^{-1}$.

5(b)
(1S,5R,6R,7R)-6-[(E)-3-Oxo-1-octen-6-ynyl]-7-benzoyloxy-2-oxabicyclo[3,3,0]octan-3-one At room temperature, a solution of 3.3 g. of the phosphonate produced according to Example 5(a) in 30 ml. of DME (absolute) is added dropwise to a suspension of 580 mg. of sodium hydride (50% suspension in oil) in 50 ml. of absolute DME. The mixture is agitated under argon at room temperature for 2 hours, then at −20° combined with a solution of 2.74 g. of (1S,5R,6R,7R)-6-formyl-7-benzoyloxy-2-oxabicyclo[3,3,0]-octan-3-one in 40 ml. of absolute DME. The mixture is stirred for 2 hours at −20°, neutralized with acetic acid, diluted with ether, shaken with 4% sodium bicarbonate solution and water, dried over magnesium sulfate, and evaporated under vacuum. Column chromatography of the residue on silica gel yields, with ether/pentane (8+2), 2.4 g. of the title compound as a colorless oil.

IR: 2930, 1775, 1718, 1678, 1630, 1270, 978 cm$^{-1}$.

5(c)
(1S,5R,6R,7R)-6-[(E)-(3S)-3-Hydroxy-1-octen-6-ynyl]-7-benzoyloxy-2-oxabicyclo[3,3,0]octan-3-one and (1S,5R,6R,7R)-6-[(E)-(3R)-3-Hydroxy-1-octen-6-ynyl]-7-benzoyloxy-2-oxabicyclo[3,3,0]octan-3-one A solution of 3.5 g. of the ketone prepared according to Example 5(b) in 230 ml. of DME is combined at 5° with 230 ml. of ethereal zinc borohydride solution; the mixture is stirred for 5 hours. After the gentle addition of water, the mixture is diluted with ether, shaken with brine, dried over magnesium sulfate, and evaporated under vacuum. After column chromatography on silica gel with ether/pentane (9+1), there is first eluted 1.2 g. of the α-alcohol (3S-configuration) and then 950 mg. of the corresponding β-alcohol (3R-configuration) is obtained, both products in the form of colorless oils.

IR (α-alcohol): 3610, 3500, 2965, 1770, 1719, 1605, 976 cm$^{-1}$.

IR (β-alcohol): spectrum almost identical to that of the α-alcohol.

5(d)
(1S,5R,6R,7R)-6-[(E)-(3S)-3-Hydroxy-1-octen-6-ynyl]-7-hydroxy-2-oxabicyclo[3,3,0]-octan-3-one In analogy to Example 1(e), 1.1 g. of the α-alcohol prepared according to Example 5(c) yields 700 mg. of the title compound as a colorless oil.

IR: 3610, 3450, 2965, 1772, 976 cm$^{-1}$.

5(e)
(1S,5R,6R,7R)-6-[(E)-(3S)-3-(Tetrahydropyran-2-yloxy)-1-octen-6-ynyl]-7-(tetrahydropyran-2-yloxy)-2-oxabicyclo[3,3,0]octan-3-one Analogously to Example 1(f), 1.74 g. of the compound prepared according to Example 5(d) yields 2.68 g. of the title compound as a colorless oil.

IR: 2955, 1768, 976 cm$^{-1}$.

5(f)
(2RS,3aR,4R,5R,6aS,3′S)-4-[(E)-1-Octen-6-ynyl]-2-hydroxy-3′,5-bis(tetrahydropyran-2-yloxy)perhydrocyclopenta[b]furan Analogously to Example 1(g), 2.6 g. of the compound produced according to Example 5(e) yields 2.5 g. of the lactol as a colorless oil.

IR: 3600, 3400, 2955, 978 cm$^{-1}$.

5(g)
(5Z,13E)-(9S,11R,15S)-9-Hydroxy-11,15-bis(tetrahydropyran-2-yloxy)-5,13-prostadien-18-ynoic Acid Analogously to Example 1(h), 2.4 g. of the lactol prepared according to Example 5(f) yields 1.85 g. of the title compound as a colorless oil.

IR: 3610, 3400, 2940, 1710, 978 cm$^{-1}$.

5(h)
(5Z,13E)-(11R,15S)-9-Oxo-11,15-bis(tetrahydropyran-2-yloxy)-5,13-prostadien-18-ynoic Acid In analogy to Example 1(i), 900 mg. of the compound obtained according to Example 5(g) yields 680 mg. of the title compound as a colorless oil.

IR: 3600, 2950, 1738, 1710, 976 cm$^{-1}$.

EXAMPLE 6
(5Z,13E)-(9S,11R,15S)-9,11,15-Trihydroxy-5,13-prostadien-18-ynoic Acid Analogously to Example 2, 310 mg. of the compound prepared according to Example 5(g) yields 170 mg. of the title compound as a colorless oil.

IR: 3605, 3470 (broad), 2935, 1710, 977 cm$^{-1}$.

EXAMPLE 7
(5Z,13E)-(11R,15RS)-11,15-Dihydroxy-15-methyl-9-oxo-5,13-prostadien-18-ynoic Acid 500 mg. of (5Z,13E)-(11R,15RS)-15-methyl-9-oxo-11,15-bis(tetrahydropyran-2-yloxy)-5,13-prostadien-18-ynoic acid is agitated for 16 hours at 20° with 15 ml. of a mixture of glacial acetic acid/water/THF (65/35/10), then evaporated under vacuum, and the remainder purified by column chromatography on silica gel. With methylene chloride/5% methanol, 260 mg. of the title compound is obtained in the form of an oil.

IR: 3600, 3400 (broad), 2965, 1740, 1710, 978 cm$^{-1}$.

The starting material for the above compound is prepared as set forth below:

7(a)
(1S,5R,6R,7R)-6-[(E)-(3RS)-3-Hydroxy-3-methyl-1-octen-6-ynyl]-7-benzoyloxy-2-oxabicyclo[3,3,0]octan-3-one At −60°, 90 ml. of an ethereal methylmagnesium bromide solution (prepared from 0.3 mole of magnesium) is added to a solution of 12.1 g. of the ketone prepared according to Example 5(b) in 460 ml. of absolute THF; the mixture is agitated for 15 minutes, then poured into 500 ml. of saturated ammonium chloride solution, stirred for 10 minutes at 20°, extracted four times with respectively 150 ml. of ether; the organic extract is washed neutral with water, dried over magnesium sulfate, and evaporated under vacuum. After purification by column chromatography on silica gel, 11.4 g. of the title compound is obtained with ether as a colorless oil.

IR: 3600, 3500, 2965, 1770, 1720, 976 cm$^{-1}$.

7(b)
(1S,5R,6R,7R)-6-[(E)-(3RS)-3-Hydroxy-3-methyl-1-octen-6-ynyl]-7-hydroxy-2-oxabicyclo[3,3,0]-octan-3-one Analogously to Example 1(e), 8.5 g. of the compound produced as set forth in Example 7(a) yields 5.10 g. of the title compound as a colorless oil.

IR: 3600, 3500, 2965, 1772, 975 cm$^{-1}$.

7(c)
(1S,5R,6R,7R)-6-[(E)-(3RS)-3-Methyl-3-tetrahydropyran-2-yloxy)-1-octen-6-ynyl]-7-(tetrahydropyran-2-yloxy)-2-oxabicyclo-[3,3,0]octan-3-one In analogy to Example 1(f), 4.3 g. of the diol obtained according to Example 7(b) yields 6.4 g. of the bis-THP ether as a colorless oil.

IR: 2955, 1770, 978 cm$^{-1}$.

7(d)
(2RS,3aR,4R,5R,6aS,3'RS)-4-[(E)-3-Methyl-1-octen-6-ynyl]-2-hydroxy-3',5-bis(tetrahydropyran-2-yloxy)perhydrocyclopenta[b]furan Analogously to Example 1(g), 6.3 g. of the compound produced according to Example 7(c) yields 6.2 g. of the lactol as a colorless oil.

IR: 3600, 3450, 2955, 978 cm$^{-1}$.

7(e)
(5Z,13E)-(9S,11R,15RS)-9-Hydroxy-15-methyl-11,15-bis(tetrahydropyran-2-yloxy)-5,13-prostadien-18-ynoic Acid Analogously to Example 1(h), 6.1 g. of the compound prepared in accordance with Example 7(d) yields 4.2 g. of the title compound as a colorless oil.

IR: 3600, 2935, 1710, 976 cm$^{-1}$.

7(f)
(5Z,13E)-(11R,15RS)-15-Methyl-9-oxo-11,15-bis(tetrahydropyran-2-yloxy)-5,13-prostadien-18-ynoic Acid In analogy to Example 1(i), 3.6 g. of the acid produced according to Example 7(e) yields 2.9 g. of the 9-oxo compound as a colorless oil.

IR: 3600, 2950, 1740, 1710, 977 cm$^{-1}$.

EXAMPLE 8

(5Z,13E)-(9S,11R,15RS)-15-Methyl-9,11,15-trihydroxy-5,13-prostadien-18-ynoic Acid Analogously to Example 2, 600 mg. of the compound obtained by following Example 7(e) yields 290 mg. of the title compound in the form of an oil.

IR: 3610, 3430, 2935, 1710, 978 cm$^{-1}$.

EXAMPLE 9

(5Z,13E)-(15R)-16,16-Dimethyl-15-hydroxy-9-oxo-5,13-prostadien-18-ynoic Acid

At 20°, 390 mg. of (5Z,13E)-(15R)-16,16-dimethyl-9-oxo-15-(tetrahydropyran-2-yloxy)-5,13-prostadien-18-ynoic acid is agitated for 16 hours with 10 ml. of a mixture of glacial acetic acid/water/THF (65/35/10); the mixture is evaporated under vacuum and the residue purified by column chromatography on silica gel. With methylene chloride/5% methanol, 305 mg. of the title compound is obtained as a colorless oil.

IR: 3600, 3450, 2962, 1737, 1710, 976 cm$^{-1}$.

The starting material for the above compound is prepared as follows:

9(a)
(1S,5R,6R)-6-[(E)-4,4-Dimethyl-3-oxo-1-octen-6-ynyl]-2-oxabicyclo[3,3,0]octan-3-one At 20°, a solution of 11.5 g. of the phosphonate prepared as set forth in Example 1(b) in 80 ml. of DME is added dropwise to a suspension of 2 g. of sodium hydride (50% suspension in oil) in 160 ml. of DME; the mixture is agitated for 2 hours under argon. Then, the mixture is combined at −20° with a solution of 6.5 g. of (1S,5R,6S)-6-formyl-2-oxabicyclo[3,3,0]octan-3-one [E. J. Corey et al., J. Org. Chem. 39:256 (1974)] in 80 ml. of DME, and the mixture is agitated for 2 hours at this temperature, whereupon it is neutralized with acetic acid, diluted with ether, shaken with 4% sodium bicarbonate solution and water, dried over magnesium sulfate, and evaporated under vacuum. After purification by chromatography on silica gel, 6.9 g. of the title compound is obtained with ether as a colorless oil.

IR: 2970, 1768, 1688, 1624, 982 cm$^{-1}$.

9(b)
(1S,5R,6R)-6-[(E)-(3R)-4,4-Dimethyl-3-hydroxy-1-octen-6-ynyl]-2-oxabicyclo[3,3,0]octan-3-one and (1S,5R,6R)-6-[(E)-(3S)-4,4-Dimethyl-3-hydroxy-1-octen-6-ynyl]-2-oxabicyclo[3,3,0]octan-3-one A solution of 6.8 g. of the ketone obtained according to Example 9(a) in 680 ml. of DME is combined at 5° with 680 ml. of an ethereal zinc borohydride solution. After 3.5 hours, 68 ml. of water is added gently to the reaction mixture and the latter stirred for 30 minutes at 20°, then filtered, the filtrate shaken with brine, dried over magnesium sulfate, and evaporated under vacuum. After column chromatography on silica gel with ether/hexane (8+2), 2.5 g. of the α-alcohol is first of all eluted (3R-configuration), and then 1 g. of the corresponding β-alcohol is obtained (3S-configuration), both compounds in the form of colorless oils.

IR (α-alcohol): 3600, 3560, 2960, 1765, 1165, 975 cm$^{-1}$.

IR (β-alcohol): practically congruent with that of the α-alcohol.

9(c)
(1S,5R,6R)-6-[(E)-(3R)-4,4-Dimethyl-3-tetrahydropyran-2-yloxy)-1-octen-6-ynyl]-2-oxabicyclo[3,3,0]octan-3-one At 5°, 2.5 g. of the α-alcohol produced according to Example 9(b) is agitated with 985 mg. of dihydropyran and 8 mg. of p-toluenesulfonic acid in 40 ml. of methylene chloride for 40 minutes. After dilution with ether, the mixture is shaken with 4% sodium bicarbonate solution and water, dried over magnesium sulfate, and evaporated under vacuum, thus obtaining 3.3 g. of the title compound as a colorless oil.

IR: 2950, 1770, 978 cm$^{-1}$.

9(d)
(2RS,3aR,4R,6aS)-4-[(E)-(3R)-4,4-Dimethyl-3-(tetrahydropyran-2-yloxy)-1-octen-6-ynyl]-2-hydroxyperhydrocyclopenta[b]furan Under argon, 33.5 ml. of a 20% solution of diisobutyl aluminum hydride in toluene is added dropwise to a solution, cooled to −70°, of 3.35 g. of the THP ether prepared according to Example 9(c) in 180 ml. of toluene. The mixture is stirred for 30 minutes at −70°, and then the reaction is terminated by the dropwise addition of isopropanol. The mixture is combined with 16 ml. of water, the cooling bath is removed, the mixture is stirred for 60 minutes, filtered, and evaporated under vacuum, thus obtaining 3.30 g. of the title compound as a colorless oil.

IR: 3600, 3520, 2950, 978 cm$^{-1}$.

9(e)
(5Z,13E)-(9S,15R)-16,16-Dimethyl-9-hydroxy-15-(tetrahydropyran-2-yloxy)-5,13-prostadien-18-ynoic Acid At 15°, 36 ml. of a solution of methanesulfinylmethyl sodium in DMSO [preparation: see Example 1(h)] is added dropwise to a solution of 8.3 g. of 4-carboxybutyltriphenylphosphonium bromide in 32 ml. of DMSO; the mixture is stirred for 15 minutes at 20° and then a solution of 1.70 g. of the lactol obtained according to Example 9(d) in 18 ml. of DMSO is added dropwise to the red ylene solution. The mixture is then agitated for 2 hours at 50° under argon, poured on 200 ml. of ice water, and extracted three times with a mixture of ether/ethyl acetate (1+1). The aqueous phase is acidified with 10% citric acid solution to pH 5-6 and extracted three times with ethyl acetate. This extract is shaken with brine, dried with magnesium sulfate, and evaporated under vacuum. Chromatography of the residue on silica gel with ether/ethyl acetate (8+2) yields 1.35 g. of the title compound as a colorless oil.

IR: 3600, 2950, 1710, 976 cm$^{-1}$.

9(f)
(5Z,13E)-(15R)-16,16-Dimethyl-9-oxo-15-(tetrahydropyran-2-yloxy)-5,13-prostadien-18-ynoic Acid At −30°, 0.8 ml. of Jones reagent is added to a solution of 610 mg. of the compound prepared according to Example 9(e) in 18 ml. of acetone; the mixture is stirred for 30 minutes, the excess reagent is destroyed with isopropanol, diluted with ether, shaken neutral with brine, dried over magnesium sulfate, and evaporated under vacuum. Purification by chromatography on silica gel with pentane/ethyl acetate (1+1) yields 490 mg. of the title compound as a colorless oil.

IR: 3500–3200 (broad), 2955, 1735, 1710, 980 cm$^{-1}$.

EXAMPLE 10
(5Z,13E)-(9S,15R)-16,16-Dimethyl-9,15-dihydroxy-5,13-prostadien-18-ynoic Acid At room temperature, 310 mg. of the compound produced as set forth in Example 9(e) is agitated for 16 hours with 9 ml. of a mixture of glacial acetic acid/water/THF (65/35/10), then evaporated under vacuum, and the residue is purified by column chromatography on silica gel. With methylene chloride/5% methanol, 210 mg. of the title compound is obtained as a colorless oil.

IR: 3600, 2955, 1710, 978 cm$^{-1}$.

EXAMPLE 11
(5Z,13E)-(15S,16RS)-16-Methyl-15-hydroxy-9-oxo-5,13-prostadien-18-ynoic Acid 410 mg. of (5Z,13E)-(15S,16RS)-16-methyl-9-oxo-15-(tetrahydropyran-2-yloxy)-5,13-prostadien-18-ynoic acid is agitated at 23° for 16 hours with 11 ml. of a mixture of glacial acetic acid/water/THF (65/35/10); the mixture is evaporated under vacuum, and the residue is purified by column chromatography on silica gel. With methylene chloride/5% methanol, 290 mg. of the title compound is obtained as a colorless oil.

IR: 3600, 3460, 2960, 1738, 1710, 978 cm$^{-1}$.

The starting material for the above compound is prepared as follows:

11(a)
(1S,5R,6R)-6-[(E)-(4RS)-4-Methyl-3-oxo-1-octen-6-ynyl]-2-oxabicyclo[3,3,0]octan-3-one Analogously to Example 9(a), 3.2 g. of (1S,5R,6S)-6-formyl-2-oxabicyclo[3,3,0]octan-3-one and 5.7 g. of the phosphonate produced according to Example 3(b) yield 3.3 g. of the title compound as a colorless oil.

IR: 2965, 1770, 1690, 1625, 980 cm$^{-1}$.

11(b)
(1S,5R,6R)-6-[(E)-(3S,4RS)-4-Methyl-3-hydroxy-1-octen-6-ynyl]-2-oxabicyclo[3,3,0]octan-3-one and (1S,5R,6R)-6-[(E)-(3R,4RS)-4-Methyl-3-hydroxy-1-octen-6-ynyl]-2-oxabicyclo[3,3,0]octan-3-one A solution of 3.3 g. of the ketone obtained according to Example 11(a) in 340 ml. of DME is combined at 5° with 340 ml. of ethereal zinc borohydride solution. After 4 hours, 320 ml. of water is gently added thereto, the mixture is stirred for 30 minutes at 20°, filtered, the filtrate shaken with brine, dried over magnesium sulfate, and evaporated under vacuum. After column chromatography on silica gel with ether/hexane (8+2), there is first eluted 1.2 g. of the α-alcohol (3S-configuration), and then 0.7 g. of the corresponding β-alcohol (3R-configuration) is obtained, both products in the form of colorless oils.

IR (α-alcohol): 3610, 3500, 2960, 1765, 976 cm$^{-1}$.

IR (β-alcohol): spectrum almost identical to that of the α-alcohol.

11(c)
(1S,5R,6R)-6-[(E)-(3S,4RS)-4-Methyl-3-(tetrahydropyran-2-yloxy)-1-octen-6-ynyl]-2-oxabicyclo[3,3,0]octan-3-one Analogously to Example 9(c), 1.2 g. of the α-alcohol prepared in accordance with Example 11(b) yields 1.50 g. of the title compound as a colorless oil.

IR: 2955, 1772, 978 cm$^{-1}$.

11(d)
(2RS,3aR,4R,6aS)-4-[(E)-(3S,4RS)-4-Methyl-3-tetrahydropyran-2-yloxy)-1-octen-6-ynyl]-2-hydroxyperhydrocyclopenta[b]furan In analogy to Example 9(d), 1.4 g. of the compound produced according to Example 11(c) yields 1.36 g. of the title compound as a colorless oil.

IR: 3600, 3500, 2955, 976 cm$^{-1}$.

11(e)
(5Z,13E)-(9S,15S,16RS)-9-Hydroxy-16-methyl-15-(tetrahydropyran-2-yloxy)-5,13-prostadien-18-ynoic Acid Analogously to Example 9(e), 1.3 g. of the lactol obtained according to Example 11(d) yields 1.05 g. of the title compound as a colorless oil.

IR: 3610, 2955, 1710, 976 cm$^{-1}$.

11(f)
(5Z,13E)-(15S,16RS)-16-Methyl-9-oxo-15-(tetrahydropyran-2-yloxy)-5,13-prostadien-18-ynoic Acid In analogy to Example 9(f), 0.9 g. of the compound obtained by following Example 11(e) yields 0.61 g. of the title compound as a colorless oil.

IR: 3510–3200 (broad), 2955, 1736, 1710, 978 cm$^{-1}$.

EXAMPLE 12
(5Z,13E)-(9S,15S,16RS)-9,15-Dihydroxy-16-methyl-5,13-prostadien-18-ynoic Acid Analogously to Example 10, 240 mg. of the compound prepared according to Example 11(e) yields 145 mg. of the title compound as a colorless oil.

IR: 3600, 2960, 1710, 976 cm$^{-1}$.

EXAMPLE 13

(5Z,13E)-(15S)-15-Hydroxy-9-oxo-5,13-prostadien-18-ynoic Acid 320 mg. of (5Z,13E)-(15S)-9-oxo-15-(tetrahydropyran-2-yloxy)-5,13-prostadien-18-ynoic acid is agitated for 16 hours at room temperature with 8 ml. of a mixture of glacial acetic acid/water/THF (65/35/10), then evaporated under vacuum, and the residue purified by column chromatography on silica gel. With methylene chloride/5% methanol, 210 mg. of the title compound is obtained as a colorless oil.

IR: 3600, 3450, 2963, 1737, 1710, 978 cm$^{-1}$.

The starting material for the above compound is prepared as follows:

13(a)
(1S,5R,6R)-6-[(E)-3-Oxo-1-octen-6-ynyl]-2-oxabicyclo[3,3,0]octan-3-one Analogously to Example 9(a), 2.8 g. of the phosphonate produced according to Example 5(a) yields 1.7 g. of the title compound as a colorless oil.

IR: 2967, 1768, 1690, 1625, 980 cm$^{-1}$.

13(b)
(1S,5R,6R)-6-[(E)-(3S)-3-Hydroxy-1-octen-6-ynyl]-2-oxabicyclo[3,3,0]octan-3-one and
(1S,5R,6R)-6-[(E)-(3R)-3-Hydroxy-1-octen-6-ynyl]-2-oxabicyclo[3,3,0]octan-3-one Analogously to Example 11(b), 6 g. of the compound prepared as set forth in Example 13(a) yields 2.3 g. of the nonpolar α-alcohol (3S-configuration), as well as 1.95 g. of the polar β-alcohol (3R-configuration), both in the form of oils.

IR (α-alcohol): 3600, 3520, 2955, 1770, 976 cm$^{-1}$.

IR (β-alcohol): the spectrum is almost identical to that of the α-alcohol.

13(c)
(1S,5R,6R)-6-[(E)-(3S)-3-(Tetrahydropyran-2-yloxy)-1-octen-6-ynyl]-2-oxabicyclo[3,3,0]-octan-3-one Analogously to Example 9(c), 2.15 g. of the compound produced according to Example 13(b) yields 2.53 g. of the title compound in the form of an oil.

IR: 2960, 1770, 978 cm$^{-1}$.

13(d)
(2RS,3aR,4R,6aS)-4-[(E)-(3S)-3-Tetrahydropyran-2-yloxy)-1-octen-6-ynyl]-2-hydroxyperhydrocyclopenta[b]furan An analogy to Example 9(d), 2.50 g. of the compound prepared according to Example 13(c) yields 2.41 g. of the lactol as a colorless oil.

IR: 3600, 3490, 2958, 978 cm$^{-1}$.

13(e)
(5Z,13E)-(9S,15S)-9-Hydroxy-15-(Tetrahydropyran-2-yloxy)-5,13-prostadien-18-ynoic Acid Analogously to Example 9(e), 2.40 g. of the compound produced according to Example 13(d) yields 1.95 g. of the title compound as colorless oil.

IR: 3600, 2960, 1712, 978 cm$^{-1}$.

13(f)
(5Z,13E)-(15S)-9-Oxo-15-(tetrahydropyran-2-yloxy)-5,13-prostadien-18-ynoic Acid Analogously to Example 9(f), 1.10 g. of the compound obtained in accordance with Example 13(e) yields 0.91 g. of the title compound as an oil.

IR: 3600, 2955, 1740, 1710, 978 cm$^{-1}$.

EXAMPLE 14

(5Z,13E)-(9S,15S)-9,15-Dihydroxy-5,13-prostadien-18-ynoic Acid

In analogy to Example 10, 250 mg. of the compound prepared according to Example 13(e) yields 130 mg. of the title compound as a colorless oil.

IR: 3600, 3490, 1710, 975 cm$^{-1}$.

EXAMPLE 15

(5Z,13E)-(15RS)-15-Hydroxy-15-methyl-9-oxo-5,13-prostadien-18-ynoic Acid 300 mg. of (5Z,13E)-(15RS)-15-methyl-9-oxo-15-(tetrahydropyran-2-yloxy)-5,13-prostadien-18-ynoic acid is agitated for 16 hours at room temperature with 8 ml. of a mixture of glacial acetic acid/water/THF (65/35/10); the mixture is then evaporated under vacuum, and the residue is purified by chromatography on silica gel. With methylene chloride/5% methanol, 205 mg. of the title compound is obtained as a colorless oil.

IR: 3600, 3450, 2955, 1740, 1712, 975 cm$^{-1}$.

The starting material for the above compound is obtained as follows:

15(a)
(1S,5R,6R)-6-[(E)-(3RS)-3-Hydroxy-3-methyl-1-octen-6-ynyl]-2-oxabicyclo[3,3,0]octan-3-one Analogously to Example 7(a), 8 g. of (1S,5R,6R)-6-[(E)-3-oxo-1-octen-6-ynyl]-2-oxabicyclo[3,3,0]octan-3-one [preparation see Example 13(a)] is reacted with methylmagnesium bromide, thus obtaining 6.8 g. of the title compound as a colorless oil.

IR: 3600, 2952, 1765, 975 cm$^{-1}$.

15(b)
(1S,5R,6R)-6-[(E)-(3RS)-3-Methyl-3-(tetrahydropyran-2-yloxy)-1-octen-6-ynyl]-2-oxabicyclo[3,3,0]octan-3-one In analogy to Example 9(c), 6 g. of the compound obtained according to Example 15(a) yields 7.1 g. of the THP ether in the form of an oil.

IR: 2955, 1768, 980 cm$^{-1}$.

15(c)
(2RS,3aR,4R,6aS)-4-[(E)-(3RS)-3-Methyl-3-(tetrahydropyran-2-yloxy)-1-octen-6-ynyl]-2-hydroxyperhydrocyclopenta[b]furan Analogously to Example 9(d), 7.0 g. of the THP ether prepared according to Example 15(b) yields 6.85 g. of the lactol as a colorless oil.

IR: 3600, 3505, 2950, 980 cm$^{-1}$.

15(d)
(5Z,13E)-(9S,15RS)-9-Hydroxy-15-methyl-15-(tetrahydropyran-2-yloxy)-5,13-prostadien-18-ynoic Acid Analogously to Example 9(e), 5.95 g. of the lactol prepared according to Example 15(c) yields 5.10 g. of the title compound as a colorless oil.

IR: 3600, 2955, 1710, 978 cm$^{-1}$.

15(e)
(5Z,13E)-(15RS)-15-Methyl-9-oxo-15-(tetrahydropyran-2-yloxy)-5,13-prostadien-18-ynoic Acid Analogously to Example 9(f), 3.0 g. of the compound prepared according to Example 15(d) yields 2.55 g. of the title compound as a colorless oil.
IR: 3600, 2955, 1738, 1710, 978 cm$^{-1}$.

EXAMPLE 16
(5Z,13E)-(9S,15RS)-9,15-Dihydroxy-15-methyl-5,13-prostadien-18-ynoic Acid Analogously to Example 10, 300 mg. of the compound obtained as set forth in Example 15(d) yields 210 mg. of the title compound as a colorless oil.
IR: 3600, 3450, 2955, 1710, 976 cm$^{-1}$.

EXAMPLE 17
(5Z,10Z,13E)-(15R)-16,16-Dimethyl-15-hydroxy-9-oxo-(5,10,13)-prostatrien-18-ynoic Acid A mixture of 220 mg. of the prostadienoic acid prepared according to Example 1 with 15 ml. of a 90% aqueous acetic acid is agitated for 16 hours at 55°. The mixture is then evaporated under vacuum and the residue purified by column chromatography on silica gel. With methylene chloride/3% isopropanol, 140 mg. of the title compound is obtained as a colorless oil.
IR: 3600, 3410 (broad), 2940, 1705, 1588, 972 cm$^{-1}$.

EXAMPLE 18
(5Z,10Z,13E)-(15S,16RS)-15-Hydroxy-16-methyl-9-oxo-(5,10,13)-prostatrien-18-ynoic Acid Analogously to Example 17, 180 mg. of the prostadienoic acid prepared according to Example 3 yields 110 mg. of the title compound as a colorless oil.
IR: 3600, 3400 (broad), 2945, 1703, 1588, 975 cm$^{-1}$.

EXAMPLE 19
(5Z,10Z,13E)-(15S)-15-Hydroxy-9-oxo-(5,10,13)-prostatrien-18-ynoic Acid Analogously to Example 17, 250 mg. of the compound obtained according to Example 5 yields 160 mg. of the title compound as a colorless oil.
IR: 3605, 3400 (broad), 2935, 1705, 1588, 976 cm$^{-1}$.

EXAMPLE 20
(5Z,10Z,13E)-(15RS)-15-Hydroxy-15-methyl-9-oxo-(5,10,13)-prostatrien-18-ynoic Acid In analogy to Example 17, 180 mg. of the prostadienoic acid prepared according to Example 7 yields 95 mg. of the title compound as a colorless oil.
IR: 3600, 3400 (broad), 2940, 1704, 1588, 975 cm$^{-1}$.

EXAMPLE 21
(5Z,13E)-(11R,15R)-15-Hydroxy-9-oxo-11,16,16-trimethyl-5,13-prostadien-18-ynoic Acid 300 mg. of (5Z,13E)-(11R,15R)-9-oxo-15-(tetrahydropyran-2-yloxy)-11,16,16-trimethyl-5,13-prostadien-18-ynoic acid is agitated for 16 hours at room temperature with 10 ml. of a mixture of glacial acetic acid/water/THF (65/35/10); the reaction mixture is evaporated under vacuum and the residue purified by chromatography on silica gel. With methylene chloride/2% methanol, 180 mg. of the title compound is obtained as a colorless oil.
IR: 3600, 2945, 1740, 1710, 978 cm$^{-1}$.

The starting material for the above compound is produced as set forth below:

21(a) Methyl Ester of (1R,2S,3R)-2-Benzyloxymethyl-3-methyl-5-oxocyclopentylacetic Acid 1.39 g. of copper(I) iodide is suspended in 20 ml. of ether and combined at 0° with 8 ml. of a 1.6-molar ethereal solution of methyllithium. After 15 minutes, the mixture is cooled to −40° and a solution of 1 g. of the methyl ester of 2-benzyloxymethyl-5-oxocyclopent-3-enylacetic acid (P. Crabbe et al., J. Chem. Soc. Perkin I. 1973: 810) in 15 ml. of ether is added dropwise thereto. After 45 minutes, the excess reagent is carefully destroyed with chipped ice pieces. The mixture is diluted with 200 ml. of ether, and this phase is shaken with saturated ammonium chloride solution. The ether phase is washed neutral with brine, dried over magnesium sulfate, and evaporated under vacuum, thus obtaining 1.03 g. of the title compound as an oil.
IR: 3005, 2958, 2875, 1740, 1730 cm$^{-1}$.

| CD (in dioxane): 2 [nm.] | Δ ε |
|---|---|
| (283 | 1.98) |
| 294 | 2.70 |
| 300 | 2.76 |
| (310 | 1.68) |

21(b)
(1S,5R,6S,7R)-6-Benzyloxymethyl-7-methyloxabicyclo[3,3,0]octan-3-one

A solution of 2.5 g. of the compound prepared according to Example 21(a) in 200 ml. of THF is combined at −70° under argon with 12.5 ml. of a 1-molar solution of "L-Selectrid." After 45 minutes, 7.75 ml. of 3 N sodium hydroxide solution and 3.25 ml. of 30% $H_2O_2$ solution are added thereto; the cooling bath is removed, and the mixture is agitated for 10 minutes. Subsequently, the mixture is combined with 2.5 ml. of concentrated hydrochloric acid, 100 ml. of water, and then the mixture is extracted three times with ether. The extract is washed neutral with brine, dried over magnesium sulfate, and evaporated under vacuum. After filtration over silica gel, 2.2 g. of the title compound is obtained with ether/pentane (1+1) as a colorless oil.
IR: 2960, 2933, 2870, 1765 cm$^{-1}$.

21(c)
(1S,5R,6S,7R)-6-Hydroxymethyl-7-methyl-2-oxabicyclo[3,3,0]octan-3-one 5.2 g. of the compound prepared according to Example 21(b) in 200 ml. of ethyl acetate and 50 ml. of ethanol is shaken with 1 g. of palladium (10% on carbon) for 30 minutes under a hydrogen atmosphere. The mixture is then filtered and evaporated under vacuum, thus obtaining 3.30 g. of the title compound as a colorless oil.
IR: 3600, 2960, 2935, 1768 cm$^{-1}$.

21(d)
(1S,5R,6S,7R)-6-Formyl-7-methyl-2-oxabicyclo[3,3,0]octan-3-one

At 5°, a solution of 15 g. of the compound prepared according to Example 1(c) in 500 ml. of absolute methylene chloride is added to a solution of 136 g. of freshly prepared Collins reagent in 1 l. of absolute methylene chloride. The mixture is agitated for 30 minutes, combined with 2.5 l. of ether, and shaken in succession four times with respectively 150 ml. of 4% sodium bicarbonate solution, twice with respectively 175 ml. of 10% sulfuric acid, and four times with respectively 150 ml. of brine. After drying over magnesium sulfate, the mixture is evaporated under vacuum, thus obtaining 11.2 g. of the title compound as a brown oil.

IR: 2955, 2870, 2720, 1765, 1722 cm$^{-1}$.

21(e)
(1S,5R,6R,7R)-6-[(E)-4,4-Dimethyl-3-oxo-1-octen-6-ynyl]-7-methyl-2-oxabicyclo[3,3,0]-octan-3-one Analogously to Example 9(a), 10.5 g. of the aldehyde prepared according to Example 21(d) yields 12.2 g. of the title compound as a colorless oil.

IR: 2965, 1768, 1688, 1625, 980 cm$^{-1}$.

21(f)
(1S,5R,6R,7R)-6-[(E)-(3R)-4,4-Dimethyl-3-hydroxy-1-octen-6-ynyl]-7-methyl-2-oxabicyclo[3,3,0]octan-3-one In analogy to Example 9(b), 11 g. of the ketone produced in accordance with Example 21(e) yields 4.1 g. of the title compound, as well as 3.8 g. of the corresponding β-alcohol (3S-configuration), both in the form of colorless oils.

IR: 3600, 3500, 2965, 1768, 976 cm$^{-1}$.

21(g)
(1S,5R,6R,7R)-6-[(E)-(3R)-4,4-Dimethyl-3-(tetrahydropyran-2-yloxy)-1-octen-6-ynyl]-7-methyl-2-oxabicyclo[3,3,0]octan-3-one Analogously to Example 9(c), 2.6 g. of the alcohol prepared according to Example 21(f) yields 3.4 g. of the title compound as an oil.

IR: 2960, 1768, 978 cm$^{-1}$.

21(h)
(2RS,3aR,4R,5R,6aS)-4-[(E)-(3R)-4,4-Dimethyl-3-(tetrahydropyran-2-yloxy)-1-octen-6-ynyl]-2-hydroxy-5-methylperhydrocyclopenta[b]furan Analogously to Example 9(d), 3.4 g. of the THP ether produced by following Example 21(g) yields 3.35 g. of the title compound as a colorless oil.

IR: 3600, 3520, 2950, 978 cm$^{-1}$.

21(i)
(5Z,13E)-(9S,11R,15R)-9-Hydroxy-11,16,16-trimethyl-15-(tetrahydropyran-2-yloxy)-5,13-prostadien-18-ynoic Acid In analogy to Example 9(e), 3.30 g. of the lactol produced according to Example 21(h) yields 2.95 g. of the title compound as a colorless oil.

IR: 3600, 2950, 1710, 980 cm$^{-1}$.

21(j)
(5Z,13E)-(11R,15R)-9-Oxo-11,16,16-trimethyl-15-(tetrahydropyran-2-yloxy)-5,13-prostadien-18-ynoic Acid Analogously to Example 9(f), 1.1 g. of the 9-hydroxy compound prepared according to Example 21(i) yields 0.98 g. of the 9-oxo compound as a light-yellow oil.

IR: 3500–3210, 2960, 1738, 1710, 975 cm$^{-1}$.

EXAMPLE 22
(5Z,13E)-(9S,11R,15R)-9,15-Dihydroxy-11,16,16-trimethyl-5,13-prostadien-18-ynoic Acid In analogy to Example 2, 180 mg. of the compound prepared according to Example 21(i) yields 93 mg. of the title compound as a colorless oil.

IR: 3600, 3450, 2935, 1710, 976 cm$^{-1}$.

EXAMPLE 23
(5Z,13E)-(11R,15S,16RS)-11,16-Dimethyl-15-hydroxy-9-oxo-5,13-prostadien-18-ynoic Acid 290 mg. of (5Z,13E)-(11R,15S,16RS)-11,16-dimethyl-9-oxo-15-(tetrahydropyran-2-yloxy)-(5,13)-prostadien-18-ynoic acid is agitated for 16 hours at room temperature with 9 ml. of a mixture of glacial acetic acid/water/THF (65/35/10). The reaction mixture is evaporated under vacuum and the residue purified by column chromatography on silica gel. With methylene chloride/5% methanol, 160 mg. of the title compound is obtained as a colorless oil.

IR: 3600, 3400 (broad), 2965, 1738, 1710, 976 cm$^{-1}$.

The starting material for the above compound is produced as set out below:

23(a)
(1S,5R,6R,7R)-6-[(E)-(4RS)-4-Methyl-3-oxo-1-octen-6-ynyl]-7-methyl-2-oxabicyclo[3,3,0]-octan-3-one Analogously to Example 9(a), 3.9 g. of the phosphonate produced in accordance with Example 3(b) and 3.7 g. of the aldehyde prepared according to Example 21(d) set forth hereinabove yield 3.9 g. of the title compound as a colorless oil.

IR: 2960, 1770, 1688, 1625, 979 cm$^{-1}$.

23(b)
(1S,5R,6R,7R)-6-[(E)-(3S,4RS)-3-Hydroxy-4-methyl-1-octen-6-ynyl]-7-methyl-2-oxabicyclo-[3,3,0]octan-3-one In analogy to Example 9(b), 3.8 g. of the ketone prepared according to Example 23(a) yields 1.3 g. of the title compound, as well as 0.95 g. of the corresponding β-alcohol (3R-configuration), both as colorless oils.

IR: 3610, 3500, 2965, 1770, 976 cm$^{-1}$.

23(c)
(1S,5R,6R,7R)-6-[(E)-(3S,4RS)-4-Methyl-3-(tetrahydropyran-2-yloxy)-1-octen-6-ynyl]-7-methyl-2-oxabicyclo[3,3,0]octan-3-one Analogously to Example 9(c), 1.3 g. of the alcohol prepared according to Example 23(b) yields 1.75 g. of the title compound as an oil.

IR: 2965, 1770, 976 cm$^{-1}$.

23(d)
(2RS,3aR,4R,5R,6aS)-4-[(E)-(3S,4RS)-4-Methyl-3-(tetrahydropyran-2-yloxy)-1-octen-6-ynyl]-2-hydroxy-5-methylperhydrocyclopenta[b]furan In analogy to Example 9(d), 1.7 g. of the THP ether prepared according to Example 23(c) yields 1.6 g. of the lactol as an oil.

IR: 3600, 3500, 2955, 978 cm$^{-1}$.

23(e)
(5Z,13E)-(9S,11R,15S,16RS)-11,16-Dimethyl-9-hydroxy-15-(tetrahydropyran-2-yloxy)-5,13-prostadien-18-ynoic Acid In analogy to Example 9(e), 1.5 g. of the lactol produced according to Example 23(d) yields 1.35 g. of the title compound as a colorless oil.

IR: 3600, 2950, 1710, 978 cm$^{-1}$.

23(f)
(5Z,13E)-(11R,15S,16RS)-11,16-Dimethyl-9-oxo-15-(tetrahydropyran-2-yloxy)-5,13-prostadien-18-ynoic Acid In analogy to Example 9(f), 1.2 g. of the 9-hydroxy compound prepared by following Example 23(e) yields 0.9 g. of the 9-oxo compound as a colorless oil.

IR: 3600–3200, 2965, 1738, 1710, 976 cm$^{-1}$.

EXAMPLE 24
(5Z,13E)-(11R,15RS)-11,15-Dimethyl-15-hydroxy-9-oxo-5,13-prostadien-18-ynoic Acid A solution of 450 mg. of (5Z,13E)-(11R,15RS)-11,15-dimethyl-9-oxo-15-(tetrahydropyran-2-yloxy)-5,13-prostadien-18-ynoic acid in 15 ml. of a mixture of glacial acetic acid/water/THF (65/35/10) is agitated for 16 hours at 25°. After evaporating the solvent under vacuum, the remainder is purified by chromatography on silica gel. By elution with methylene chloride containing 1–5% methanol, 305 mg. of the title compound is isolated in the form of an oil.

IR: 3600, 3490, 2945, 1740, 1708, 978 cm$^{-1}$.

The starting material for the above compound is prepared as follows:

24(a)
(1S,5R,6R,7R)-6-[(E)-3-Oxo-1-octen-6-ynyl]-7-methyl-2-oxabicyclo[3,3,0]octan-3-one Analogously to Example 9(a), the title compound is obtained as a colorless oil from (1S,5R,6S,7R)-6-formyl-7-methyl-2-oxabicyclo[3,3,0]octan-3-one [preparation see Example 21(d)] and 2-oxohept-5-ynephosphonic acid dimethyl ester [preparation see Example 5(a)].

IR: 2955, 1770, 1688, 1625, 975 cm$^{-1}$.

24(b)
(1S,5R,6R,7R)-6-[(E)-(3RS)-3-Hydroxy-3-methyl-1-octen-6-ynyl]-7-methyl-2-oxabicyclo[3,3,0]-octan-3-one Analogously to Example 7(a), 4.0 g. of the ketone produced according to Example 24(a) yields 3.35 g. of the title compound as a colorless oil.

IR: 3600, 2950, 1770, 975 cm$^{-1}$.

24(c)
(1S,5R,6R,7R)-6-[(E)-(3RS)-3-Methyl-3-(tetrahydropyran-2-yloxy)-1-octen-6-ynyl]-7-methyl-2-oxabicyclo[3,3,0]octan-3-one A solution of 3.20 g. of the tertiary alcohol produced according to Example 24(b) in 100 ml. of methylene chloride is combined at 0° with 2.5 g. of dihydropyran and 50 mg. of p-toluenesulfonic acid and agitated for 30 minutes. After dilution with 200 ml. of methylene chloride, the reaction mixture is shaken with sodium bicarbonate solution and brine, dried over magnesium sulfate, and evaporated under vacuum. Filtration of the residue over silica gel with ether/pentane (7+3) yields 3.45 g. of the THP ether as a colorless oil.

IR: 2955, 1770, 980 cm$^{-1}$.

24(d)
(2RS,3aR,4R,5R,6aS)-4-[(E)-(3RS)-3-Methyl-3-(tetrahydropyran-2-yloxy)-1-octen-6-ynyl]-2-hydroxy-5-methylperhydrocyclopenta[b]furan In analogy to Example 9(d), 3.30 g. of the THP ether prepared according to Example 24(c) yields, with diisobutyl aluminum hydride, 3.15 g. of the lactol as a colorless oil.

IR: 3600, 3510, 2955, 980 cm$^{-1}$.

24(e)
(5Z,13E)-(9S,11R,15RS)-11,15-Dimethyl-9-hydroxy-15-(tetrahydropyran-2-yloxy)-5,13-prostadien-18-ynoic Acid Analogously to Example 9(e), 2.85 g. of the lactol prepared according to Example 24(d) yields 2.20 g. of the title compound as a light-yellow oil.

IR: 3600, 3300 (broad), 2955, 1710, 980 cm$^{-1}$.

24(f)
(5Z,13E)-(11R,15RS)-11,15-Dimethyl-9-oxo-15-tetrahydropyran-2-yloxy)-5,13-prostadien-18-ynoic Acid Analogously to Example 9(f), 1.76 g. of the 9-hydroxy compound prepared according to Example 24(e) yields, by oxidation with Jones reagent, 1.40 g. of the 9-oxo compound as a light-yellow oil.

IR: 3600, 3300 (broad), 2960, 1740, 1712, 980 cm$^{-1}$.

EXAMPLE 25
(13E)-(11R,15R)-16,16-Dimethyl-11,15-dihydroxy-9-oxo-13-prosten-18-ynoic Acid 290 mg. of (13E)-(11R,15R)-16,16-dimethyl-11-hydroxy-9-oxo-15-(tetrahydropyran-2-yloxy)-13-prosten-18-ynoic acid is agitated for 16 hours at room temperature with 8 ml. of a mixture of glacial acetic acid/water/THF (65/35/10), evaporated under vacuum, and the residue purified by column chromatography on silica gel. With methylene chloride/5% methanol, 185 mg. of the title compound is obtained as a colorless oil.

IR: 3600, 2965, 1740, 1710, 976 cm$^{-1}$.

The starting material for the above compound is prepared as follows:

25(a)
(9S,11R)-9,11-Bis(acetoxy)-12-formyl-13,14,15,16,17,18,19,20-octanorprostanoic Acid Methyl Ester 5.3 g. of (5Z)-(9S,11R)-9,11-bis(acetoxy)-12-formyl-13,14,15,16,17,18,19,20-octanor-5-prostenoic acid methyl ester (preparation see DOS [German Unexamined Laid-Open Application] 2,517,771.3, page 32) in 200 ml. of ethyl acetate is shaken with 400 mg. of palladium (10% on carbon) for 2 hours under a hydrogen atmosphere, filtered, and evaporated at 25° under vacuum, thus obtaining 5.2 g. of the title compound as a light-yellow oil; the product is uniform as determined by thin-layer chromatography.

IR: 2960, 2730, 1730 (broad), 1245 cm$^{-1}$.

25(b)
(13E)-(9S,11R)-9,11-Bis(acetoxy)-16,16-dimethyl-15-oxo-13-prosten-18-ynoic Acid Methyl Ester At room temperature, a solution of 2.70 g. of the phosphonate produced according to Example 1(b) in 10 ml. of DME is added dropwise to a suspension of 530 mg. of sodium hydride (50% suspension in oil) in 70 ml. of DME, and the mixture is stirred for 2 hours at 20° under argon. Thereafter, the mixture is combined at −20° with a solution of 3.50 g. of the aldehyde prepared according to Example 25(a) in 40 ml. of DME. The mixture is stirred for 1.5 hours at −10°, neutralized with acetic acid, diluted with ether, shaken with 4% sodium bicarbonate solution and water, dried over magnesium sulfate, and evaporated under vacuum. After purification by column chromatography over silica gel, 3.41 g. of the unsaturated ketone is obtained with ether/pentane (1+1) as a colorless oil.

IR: 2960, 1730, 1690, 1630, 1245, 976 cm$^{-1}$.

25(c)

(13E)-(9S,11R,15R)-9,11-Bis(acetoxy)-16,16-dimethyl-15-hydroxy-13-prosten-18-ynoic Acid Methyl Ester A solution of 3.35 g. of the ketone prepared according to Example 25(b) in 200 ml. of DME is combined at 0° with 200 ml. of ethereal zinc borohydride solution and agitated for 3 hours. Subsequently, 10 ml. of water is carefully added thereto, and the mixture is stirred until the precipitate is well separated. After filtration and evaporation of the solution the crude product is purified by chromatography on silica gel with ether/pentane (8+2), thus obtaining as the nonpolar component first of all the 15β-hydroxy compound (15S-configuration) and as the more polar component 1.52 g. of the 15α-hydroxy compound (15R-configuration) in the form of an oil.

IR: 3600, 3500, 2965, 1735, 1245, 976 cm$^{-1}$.

25(d)

(13E)-(9S,11R,15R)-9,11-Bis(acetoxy)-16,16-dimethyl-15-(tetrahydropyran-2-yloxy)-13-prosten-18-ynoic Acid Methyl Ester 1.40 g. of the alcohol prepared according to Example 25(c) is agitated with 1 ml. of dihydropyran and 12 mg. of p-toluenesulfonic acid in 30 ml. of methylene chloride for 30 minutes at 5°. After dilution with methylene chloride, the mixture is shaken with sodium bicarbonate solution and water, dried over magnesium sulfate, and evaporated under vacuum. Filtration over silica gel with ether/pentane (3+7) yields 1.55 g. of the THP ether as a colorless oil.

IR: 2960, 1735, 1245, 978 cm$^{-1}$.

25(e)

(13E)-(9S,11R,15R)-9,11-Dihydroxy-16,16-dimethyl-15-(tetrahydropyran-2-yloxy)-13-prosten-18-ynoic Acid 1.1 g. of the THP ether prepared according to Example 25(d) is agitated for 16 hours at 25° with a solution of 1.80 g. of sodium hydroxide in 60 ml. of methanol and 10 ml. of water. The mixture is then concentrated under vacuum, diluted with 10 ml. of brine, acidified with 10% citric acid solution to pH 5, extracted three times with methylene chloride, the extract shaken once with brine, dried over magnesium sulfate, and evaporated under vacuum. After filtration over a small amount of silica gel, 650 mg. of the title compound is obtained with chloroform/10% isopropanol as a colorless oil.

IR: 3600, 3420, 2960, 1710, 978 cm$^{-1}$.

25(f)

(13E)-(11R,15R)-16,16-Dimethyl-11-hydroxy-9-oxo-15-(tetrahydropyran-2-yloxy)-13-prosten-18-ynoic Acid At room temperature, 2 g. of platinum oxide is shaken in 15 ml. of ethyl acetate for 2 hours under a hydrogen atmosphere. The hydrogen is displaced by nitrogen; the mixture is then shaken for 3 hours under an oxygen atmosphere and thereafter combined with a solution of 200 mg. of the acid prepared according to Example 25(e) in 5 ml. of ethyl acetate, and agitated for 48 hours under oxygen. The mixture is filtered, evaporated under vacuum, and the residue purified by column chromatography on silica gel. With methylene chloride/5% isopropanol, 105 mg. of the title compound is obtained as an oil.

IR: 3600, 3510, 2960, 1738, 1710, 976 cm$^{-1}$.

EXAMPLE 26

(13E)-(11R,15S,16RS)-11,15-Dihydroxy-9-oxo-16-methyl-13-prosten-18-ynoic Acid

By proceeding in accordance with Example 25, but with the use of the dimethyl ester of 3-methyl-2-oxohept-5-ynephosphonic acid [preparation: see Example 3(b)], the title compound is obtained as a colorless oil.

IR: 3600, 3510, 2955, 1740, 1710, 978 cm$^{-1}$.

EXAMPLE 27

(13E)-(11R,15RS)-11,15-Dihydroxy-15-methyl-9-oxo-13-prosten-18-ynoic Acid

From 270 mg. of (13E)-(11R,15RS)-11-hydroxy-15-methyl-9-oxo-15-(tetrahydropyran-2-yloxy)-13-prosten-18-ynoic acid and 9 ml. of a mixture of glacial acetic acid/water/THF (65/35/10), 190 mg. of the title compound is obtained as an oil in the usual way.

IR: 3600, 2965, 1738, 1710, 978 cm$^{-1}$.

The starting material for the above compound is prepared as follows:

27(a)

(13E)-(9S,11R)-9,11-Bis(acetoxy)-15-oxo-13-prosten-18-ynoic Acid Methyl Ester

Analogously to Example 25(b), 1.70 g. of the aldehyde prepared according to Example 25(a) and 1.30 g. of the phosphonate prepared according to Example 5(a) yield 1.65 g. of the title compound as a colorless oil.

IR: 2965, 1730, 1690, 1628, 1250, 978 cm$^{-1}$.

27(b)

(13E)-(9S,11R,15RS)-9,11-Bis(acetoxy)-15-hydroxy-15-methyl-13-prosten-18-ynoic Acid Methyl Ester Analogously to Example 7(a), 1.50 g. of the compound produced according to Example 27(a) yields, by reaction with methylmagnesium bromide, 1.32 g. of the title compound as an oil.

IR: 3600, 2955, 1730, 1245, 978 cm$^{-1}$.

27(c)

(13E)-(9S,11R,15RS)-9,11-Bis(acetoxy)-15-methyl-15-(tetrahydropyran-2-yloxy)-13-prosten-18-ynoic Acid Methyl Ester Analogously to Example 25(d), 1.25 g. of the compound produced in accordance with Example 27(b) yields, by reaction with dihydropyran, 1.40 g. of the THP ether as a colorless oil.

IR: 2960, 1735, 1245, 980 cm$^{-1}$.

27(d)

(13E)-(9S,11R,15RS)-9,11-Dihydroxy-15-methyl-15-(tetrahydropyran-2-yloxy)-13-prosten-18-ynoic Acid In analogy to Example 25(e), 1.25 g. of the THP ether produced in accordance with Example 27(c) yields, by reaction with sodium hydroxide solution, 705 mg. of the title compound in the form of an oil.

IR: 3600, 3350 (broad), 2955, 1712, 980 cm$^{-1}$.

27(e)

(13E)-(11R,15RS)-11-Hydroxy-15-methyl-9-oxo-15-(tetrahydropyran-2-yloxy)-13-prosten-18-ynoic Acid Analogously to Example 25(f), 600 mg. of the compound prepared by following Example 27(d) yields, by reaction with oxygen in the presence of platinum, 295 mg. of the 9-oxo compound in the form of an oil.

IR: 3600, 3405, 2955, 1740, 1710, 980 cm$^{-1}$.

EXAMPLE 28

(13E)-(15R)-16,16-Dimethyl-15-hydroxy-9-oxo-13-prosten-18-ynoic Acid 280 mg. of (13E)-(15R)-16,16-dimethyl-9-oxo-15-(tetrahydropyran-2-yloxy)-13-prosten-18-ynoic acid is agitated for 17 hours at 23° with 8 ml. of a mixture of glacial acetic acid/water/THF (65/35/10), evaporated under vacuum, and the residue purified by column chromatography on silica gel. With methylene chloride/5% methanol, 185 mg. of the title compound is obtained as a colorless oil.

IR: 3600, 3500, 1738, 1710, 978 cm$^{-1}$.

The starting material for the above compound is prepared as follows:

28(a)

(1S,5R,6S)-6-Diethoxymethyl-2-oxabicyclo-[3,3,0]octan-3-one 4.3 g. of (1S,5R,6S)-6-formyl-2-oxabicyclo-[3,3,0]octan-3-one [see Example 9(a)], 15 ml. of triethyl orthoformate, and 40 mg. of p-toluenesulfonic acid in 15 ml. of absolute ethyl alcohol are agitated for 16 hours at 20° under argon. The mixture is then diluted with ether, shaken in succession with sodium bicarbonate solution and water, dried over magnesium sulfate, and evaporated under vacuum, thus obtaining 4.8 g. of the title compound as an oil which is completely uniform as determined by thin-layer chromatography.

IR: 2960, 1770 cm.

28(b)

(2RS,3aR,4S,6aS)-4-Diethoxymethyl-2-hydroxyperhydrocyclopenta[b]furan

Under argon, 40 ml. of a 20% solution of diisobutyl aluminum hydride in toluene is added dropwise to a solution, cooled to −70°, of 4.7 g. of the acetate prepared according to Example 28(a) in 250 ml. of absolute toluene; the mixture is stirred for 30 minutes at −70° and the reaction is then terminated by the dropwise addition of isopropanol. The mixture is combined with 20 ml. of water, agitated for one hour at 20°, filtered, and evaporated under vacuum, thus obtaining 4.65 g. of the title compound as an oil.

IR: 3600, 3500, 2960 cm$^{-1}$.

28(c)

(5Z)-(9S)-13,13-Diethoxy-9-hydroxy-14,15,16,17,18,19,20-heptanor-5-prostenoic Acid Methyl Ester Analogously to Example 9(e), 4.50 g. of the lactol prepared according to Example 28(b) yields 4.75 g. of the prostenoic acid which is converted in the usual way into the methyl ester with ethereal diazomethane solution at 5°.

IR: 3600, 3500, 1730 cm$^{-1}$.

28(d)

(9S)-9-Acetoxy-12-formyl-13,14,15,16,17,18,19,20-octanorprostanoic Acid Methyl Ester 4.5 g. of the 9-alcohol prepared according to Example 28(c), 10 ml. of pyridine, and 5 ml. of acetic anhydride are agitated for 16 hours at room temperature. The mixture is evaporated to dryness under vacuum, and the residue is dissolved in 200 ml. of ethyl acetate. Then 500 mg. of palladium (5% on carbon) is added thereto and the mixture shaken for 2 hours under a hydrogen atmosphere. After filtration and evaporation of the solution, the remainder is agitated with 100 ml. of a mixture of glacial acetic acid/water/THF (65/35/10) for 16 hours at 20°, evaporated under vacuum, and the residue filtered over silica gel. With pentane/ether (7+3), 4.3 g. of the title compound is obtained as an oil.

IR: 2960, 2730, 1730, 1245 cm$^{-1}$.

28(e)

(13E)-(9S)-9-Acetoxy-16,16-dimethyl-15-oxo-13-prosten-18-ynoic Acid Methyl Ester Analogously to Example 25(b), 4 g. of the aldehyde prepared by following Example 28(d) yields, by reaction with the phosphonate produced according to Example 1(b), 4.2 g. of the title compound as an oil.

IR: 2960, 2730, 1730, 1690, 1630, 1245, 977 cm$^{-1}$.

28(f)

(13E)-(9S,15R)-9-Acetoxy-16,16-dimethyl-15-hydroxy-13-prosten-18-ynoic Acid Methyl Ester Analogously to Example 25(c), 4.1 g. of the ketone prepared according to Example 28(e) and ethereal zinc borohydride solution yield 1.85 g. of the title compound (15α-hydroxy) as an oily, more polar isomer.

IR: 3600, 3520, 2960, 1734, 1245, 978 cm$^{-1}$.

28(g)

(13E)-(9S,15R)-16,16-Dimethyl-9-hydroxy-15-(tetrahydropyran-2-yloxy)-13-prosten-18-ynoic Acid Analogously to Example 25(d), 1.6 g. of the compound prepared according to Example 28(f) yields the THP ether which is saponified according to Example 25(e) to obtain the title compound. Yield: 1.5 g. in the form of an oil.

IR: 3600, 3400, 2955, 1710, 978 cm$^{-1}$.

28(h)

(13E)-(15R)-16,16-Dimethyl-9-oxo-15-(tetrahydropyran-2-yloxy)-13-prosten-18-ynoic Acid In analogy to Example 9(f), 900 mg. of the prostenoic acid prepared according to Example 28(g) yields 750 mg. of the oxo compound in the form of an oil.

IR: 3610, 3500, 2965, 1740, 1710, 978 cm$^{-1}$.

EXAMPLE 29

(13E)-(15S,16RS)-15-Hydroxy-16-methyl-9-oxo-13-prosten-18-ynoic Acid

By proceeding according to Example 28, starting with the aldehyde prepared by following Example 28(d) and with the dimethyl ester of 3-methyl-2-oxohept-5-ynephosphonic acid, the title compound is obtained as a colorless oil.

IR: 3605, 3500, 1740, 1710, 976 cm$^{-1}$.

EXAMPLE 30

(13E)-(11R,15R)-15-Hydroxy-9-oxo-11,16,16-trimethyl-13-prosten-18-ynoic Acid

By proceeding according to Example 28, the title compound is obtained as a colorless oil, starting with the aldehyde described in Example 21(d).

IR: 3600, 3510, 1738, 1710, 976 cm$^{-1}$.

EXAMPLE 31

(13E)-(11R,15S,16RS)-11,16-Dimethyl-15-hydroxy-9-oxo-13-prosten-18-ynoic Acid

By proceeding according to Example 28, the title compound is obtained as a colorless oil, starting with the aldehyde described in Example 21(d) and using the dimethyl ester of 3-methyl-2-oxohept-5-ynephosphonic acid.

IR: 3600, 3500, 1740, 1712, 975 cm$^{-1}$.

EXAMPLE 32

(5Z,13E)-(11R,15R)-16,16-Dimethyl-11,15-dihydroxy-9-oxo-5,13-prostadien-18-ynoic Acid Methyl Ester A solution of 100 mg. of the acid prepared according to Example 1 in 10 ml. of methylene chloride is combined at 0° dropwise with an ethereal diazomethane solution. After evaporation of the solution under vacuum, the residue is filtered with methylene chloride over a small quantity of silica gel, thus obtaining 90 mg. of the methyl ester as a colorless oil.

IR: 3600, 2965, 1735, 975 cm$^{-1}$.

EXAMPLE 33

(5Z,13E)-(11R,15R)-16,16-Dimethyl-11,15-dihydroxy-9-oxo-5,13-prostadien-18-ynoic Acid Methylsulfonamide At 25°, 400 mg. of (5Z,13E)-(11R,15R)-16,16-dimethyl-9-oxo-11,15-bis(tetrahydropyran-2-yloxy)-5,13-prostadien-18-ynoic acid methylsulfonamide is agitated for 16 hours with 12 ml. of a mixture of glacial acetic acid/water/THF (65/35/10). The mixture is evaporated under vacuum and the residue purified by column chromatography on silica gel. With methylene chloride/2-5% methanol 202 mg. of the title compound is obtained in the form of an oil.

IR: 3590, 3400, 2950, 1738, 1720, 975 cm$^{-1}$.

The starting material for the above title compound is prepared as follows:

33(a)

(5Z,13E)-(9S,11R,15R)-16,16-Dimethyl-9-hydroxy-11,15-bis(tetrahydropyran-2-yloxy)-5,13-prostadien-18-ynoic Acid Methylsulfonamide At 15°-20°, 10 ml. of a solution of methanesulfinylmethyl sodium [prepared by following Example 1(h)] in absolute DMSO is added dropwise to a solution of 2.6 g. of [4-(methanesulfonylaminocarbonyl)butyl]triphenylphosphonium bromide in 10 ml. of DMSO. The mixture is stirred for 15 minutes at room temperature. A solution of 450 mg. of the lactol prepared according to Example 1(g) in 6 ml. of DMSO is added dropwise to this red ylene solution, and the mixture is stirred for 4 hours at 40°. The reaction mixture is then poured on ice water, acidified with 10% citric acid solution to pH 4, and extracted four times with respectively 40 ml. of a mixture of ether/pentane (1+1). The organic phase is shaken with brine, dried over magnesium sulfate, and evaporated under vacuum. Chromatography of the residue on silica gel yields, with the use of methylene chloride/isopropanol (9+1), 430 mg. of the title compound as a light-yellow oil.

IR: 3600, 3400, 2940, 1720, 978 cm$^{-1}$.

33(b)

(5Z,13E)-(11R,15R)-16,16-Dimethyl-9-oxo-11,15-bis(tetrahydropyran-2-yloxy)-5,13-prostadien-18-ynoic Acid Methylsulfonamide At −20°, 0.5 ml. of Jones reagent is added to a solution of 420 mg. of the compound prepared according to Example 33(a) in 14 ml. of acetone; the mixture is stirred for 30 minutes, the excess reagent is destroyed by adding isopropanol, and then the mixture is diluted with ether, washed neutral with brine, dried over magnesium sulfate, and evaporated under vacuum. By purification with the use of column chromatography on silica gel, 320 mg. of the title compound is obtained with ether in the form of a colorless oil.

IR: 1738, 1720, 978 cm$^{-1}$.

EXAMPLE 34

(5Z,13E)-(11R,15R)-16,16-Dimethyl-11,15-dihydroxy-9-oxo-5,13-prostadien-18-ynoic Acid Acetylamide 400 mg. of (5Z,13E)-(11R,15R)-16,16-dimethyl-9-oxo-11,15-bis(tetrahydropyran-2-yloxy)-5,13-prostadien-18-ynoic acid acetylamide is agitated for 16 hours at 25° with 12 ml. of a mixture of glacial acetic acid/water/THF (65/35/10), evaporated under vacuum, and the residue purified by column chromatography on silica gel. With methylene chloride/2-5% methanol, 190 mg. of the title compound is obtained as an oil.

IR: 3600, 3410, 2940, 1735, 1705, 975 cm$^{-1}$.

The starting material for the above title compound is prepared as follows:

34(a)

(5Z,13E)-(9S,11R,15R)-16,16-Dimethyl-9-hydroxy-11,15-bis(tetrahydropyran-2-yloxy)-5,13-prostadien-18-ynoic Acid Acetylamide At 15°, 10 ml. of a solution of methanesulfinylmethyl sodium in DMSO [see Example 1(h)] is added dropwise to a solution of 2.5 g. of [4-(acetylaminocarbonyl)butyl]triphenylphosphonium bromide in 10 ml. of DMSO; the mixture is stirred for 15 minutes at 20°. To the red ylene solution is added dropwise 445 mg. of the lactol prepared according to Example 1(g), dissolved in 6 ml. of DMSO, and the mixture is stirred for 4 hours at 40°, whereupon it is poured on ice water, acidified with 10% citric acid solution to pH 4, and extracted three times with ether/pentane (1+1). The extract is washed with brine, dried over magnesium sulfate, and evaporated under vacuum. After chromatography of the residue on silica gel, 410 mg. of the title compound is obtained as an oil with the use of methylene chloride/isopropanol (9+1).

IR: 3600, 3410, 2950, 1705, 980 cm$^{-1}$.

34(b)
(5Z,13E)-(11R,15R)-16,16-Dimethyl-9-oxo-11,15-bis(tetrahydropyran-2-yloxy)-5,13-prostadien-18-ynoic Acid Acetylamide 405 mg. of the compound prepared according to Example 34(a) in 14 ml. of acetone is combined at $-20°$ with 0.45 ml. of Jones reagent. After 30 minutes, the excess reagent is destroyed with isopropanol. The mixture is diluted with ether and washed neutral with brine, and then dried over magnesium sulfate and evaporated under vacuum. After purification by chromatography on silica gel, 290 mg. of the title compound is obtained with ether in the form of a colorless oil.

IR: 2950, 1740, 1718, 978 cm$^{-1}$.

EXAMPLE 35

By proceeding in accordance with Example 33 with the use of the corresponding intermediates prepared in the foregoing examples, the following methylsulfonamides are produced:

(5Z,13E)-(11R,15S,16RS)-11,15-dihydroxy-16-methyl-9-oxo-5,13-prostadien-18-ynoic acid methylsulfonamide (5Z,13E)-(11R,15RS)-11,15-dihydroxy-15-methyl-9-oxo-5,13-prostadien-18-ynoic acid methylsulfonamide (5Z,13E)-(11R,15RS)-11,15-dihydroxy-15-methyl-9-oxo-5,13-prostadien-18-ynoic acid methylsulfonamide (5Z,13E)-(15R)-16,16-dimethyl-15-hydroxy-9-oxo-5,13-prostadien-18-ynoic acid methylsulfonamide (5Z,13E)-(15S,15RS)-16-methyl-15-hydroxy-9-oxo-5,13-prostadien-18-ynoic acid methylsulfonamide (5Z,13E)-(11R,15R)-15-hydroxy-9-oxo-11,16,16-trimethyl-5,13-prostadien-18-ynoic acid methylsulfonamide (5Z,13E)-(11R,15S,16RS)-11,16-dimethyl-15-hydroxy-9-oxo-5,13-prostadien-18-ynoic acid methylsulfonamide (13E)-(15R)-16,16-dimethyl-15-hydroxy-9-oxo-13-prosten-18-ynoic acid methylsulfonamide (13E)-(15S,16RS)-15-hydroxy-16-methyl-9-oxo-13-prosten-18-ynoic acid methylsulfonamide (13E)-(11R,15R)-15-hydroxy-9-oxo-11,16,16-trimethyl-13-prosten-18-ynoic acid methylsulfonamide.

EXAMPLE 36

By proceeding according to Example 34 with the use of the corresponding intermediates prepared in the above examples, the following acetylamides are obtained:

(5Z,13E)-(11R,15S,16RS)-11,15-dihydroxy-16-methyl-9-oxo-5,13-prostadien-18-ynoic acid acetylamide (5Z,13E)-(11R,15RS)-11,15-dihydroxy-15-methyl-9-oxo-5,13-prostadien-18-ynoic acid acetylamide (5Z,13E)-(15R)-16,16-dimethyl-15-hydroxy-9-oxo-5,13-prostadien-18-ynoic acid acetylamide (5Z,13E)-(15S,16RS)-16-methyl-15-hydroxy-9-oxo-5,13-prostadien-18-ynoic acid acetylamide (5Z,13E)-(11R,15S,16RS)-11,16-dimethyl-15-hydroxy-9-oxo-5,13-prostadien-18-ynoic acid acetylamide (5Z,13E)-(11R,15R)-15-hydroxy-9-oxo-11,16,16-trimethyl-5,13-prostadien-18-ynoic acid acetylamide (13E)-(15R)-16,16-dimethyl-15-hydroxy-9-oxo-13-prosten-18-ynoic acid acetylamide (13E)-(15S,16RS)-15-hydroxy-16-methyl-9-oxo-13-prosten-18-ynoic acid acetylamide (13E)-(11R,15R)-15-Hydroxy-9-oxo-11,16,16-triemthyl-13-prosten-18-ynoic acid acetylamide.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What we claim is:

1. A prostane derivative of the formula

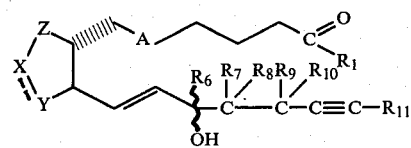

wherein $R_1$ is the residue $OR_2$ and $R_2$ is hydrogen, $C_{1-10}$ alkyl, $C_{4-10}$ cycloalkyl, phenyl, naphthyl or a 5- or 6-membered hetero monocycle containing one hetero atom of O, N or S;

A is cis-CH=CH—

Z is carbonyl or

wherein the $OR_4$ group can be in the α- or β-position and $R_4$ is H or an acyl group derived from a hydrocarbon carboxylic or sulfonic acid of up to 15 carbon atoms, tetrahydropyranyl, tetrahydrofuranyl, α-ethoxyethyl, trimethylsilyl, dimethyl-tert-butylsilyl or tri-o-benzylsilyl X=Y is

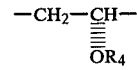

wherein $R_4$ is as defined above, —CH$_2$—CH$_2$— or

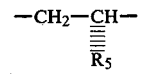

wherein $R_5$ is alkyl of 1–5 carbon atoms, if Z is carbonyl or

X=Y represents —CH=CH— if Z is carbonyl;
$R_6$, $R_7$, $R_8$, $R_9$ and $R_{10}$ each independently is hydrogen or an alkyl group of 1–5 carbon atoms; and
$R_{11}$ is alkyl of 1–5 carbon atoms;

and if $R_2$ is hydrogen, the salts thereof with physiologically compatible bases.

2. (5Z,13E)-(11R,15R)-16,16-Dimethyl-11,15-dihydroxy-9-oxo-5,13-prostadien-18-ynoic acid, a compound of claim 1.

3. (5Z,13E)-(9S,11R,15R)-16,16-Dimethyl-9,11,15-trihydroxy-5,13-prostadien-18-ynoic acid, a compound of claim 1.

4. (5Z,13E)-(11R,15S,16RS)-11,15-Dihydroxy-9-oxo-16-methyl-5,13-prostadien-18-ynoic acid, a compound of claim 1.

5. (5Z,13E)-(9S,11R,15S,16RS)-16-Methyl-9,11,15-trihydroxy-5,13-prostadien-18ynoic acid, a compound of claim 1.

6. (5Z,13E)-(11R,15S)-11,15-Dihydroxy-9-oxo-5,13-prostadien-18-ynoic acid, a compound of claim 1.

7. (5Z,13E)-(9S,11R,15S)-9,11,15-Trihydroxy-5,13-prostadien-18-ynoic acid, a compound of claim 1.

8. (5Z,13E)-(11R,15RS)-11,15-Dihydroxy-15-methyl-9-oxo-5,13-prostadien-18-ynoic acid, a compound of claim 1.

9. (5Z,13E)-(9S,11R,15RS)-15-Methyl-9,11,15-trihydroxy-5,13-prostadien-18-ynoic acid, a compound of claim 1.

10. (5Z,13E)-(15R)-16,16-Dimethyl-15-hydroxy-9-oxo-5,13-prostadien-18-ynoic acid, a compound of claim 1.

11. (5Z,13E)-(9S,15R)-16,16-Dimethyl-9,15-dihydroxy-5,13-prostadien-18-ynoic acid, a compound of claim 1.

12. (5Z,13E)-(15S,16RS)-16-Methyl-15-hydroxy-9-oxo-5,13-prostadien-18-ynoic acid, a compound of claim 1.

13. (5Z,13E)-(9S,15S,16RS)-9,15-Dihydroxy-16-methyl-5,13-prostadien-18-ynoic acid, a compound of claim 1.

14. (5Z,13E)-(15S)-15-Hydroxy-9-oxo-5,13-prostadien-18-ynoic acid, a compound of claim 1.

15. (5Z,13E)-(9S,15S)-9,15-Dihydroxy-5,13-prostadien-18-ynoic acid, a compound of claim 1.

16. (5Z,13E)-(15RS)-15-Hydroxy-15-methyl-9-oxo-5,13-prostadien-18ynoic acid, a compound of claim 1.

17. (5Z,13E)-(9S,15RS)-9,15-Dihydroxy-15-methyl-5,13-prostadien-18-ynoic acid, a compound of claim 1.

18. (5Z,10Z,13E)-(15R)-16,16-Dimethyl-15-hydroxy-9-oxo-5,10,13-prostatrien-18-ynoic acid, a compound of claim 1.

19. (5Z,10Z,13E)-(15S,16RS)-15-Hydroxy-16-methyl-9-oxo-5,10,13-prostatrien-18-ynoic acid, a compound of claim 1.

20. (5Z,10Z,13E)-(15S)-15-Hydroxy-9-oxo-5,10,13-prostatrien-18-ynoic acid, a compound of claim 1.

21. (5Z,10Z,13E)-(15RS)-15-Hydroxy-15-methyl-9-oxo-5,10,13-prostatrien-18-ynoic acid, a compound of claim 1.

22. (5Z,13E)-(11R,15R)-15-Hydroxy-9-oxo-11,16,16-trimethyl-5,13-prostadien-18-ynoic acid, a compound of claim 1.

23. (5Z,13E)-(9S,11R,15R)-9,15-Dihydroxy-11,16,16-trimethyl-5,13-prostadien-18-ynoic acid, a compound of claim 1.

24. (5Z,13E)-(11R,15S,16RS)-11,16-Dimethyl-15-hydroxy-9-oxo-5,13-prostadien-18-ynoic acid, a compound of claim 1.

25. (5Z,13E)-(11R,15RS)-11,15-Dimethyl-15-hydroxy-9-oxo-5,13-prostadien-18-ynoic acid, a compound of claim 1.

26. (5Z,13E)-(11R,15R)-16,16-Dimethyl-11,15-dihydroxy-9-oxo-5,13-prostadien-18-ynoic acid methyl ester, a compound of claim 1.

27. A pharmaceutical composition comprising an amount of a prostane derivative of claim 1 effective to induce menstruation and a pharmaceutically acceptable carrier.

28. A method for inducing menstruation in a mammal which comprises administering an amount of a prostane derivative of claim 1 effective to induce menstruation.

29. A method for triggering an abortion in a mammal which comprises administering an amount of a prostane derivative of claim 1 effective to trigger an abortion.

* * * * *